(12) United States Patent
Mahmoudi et al.

(10) Patent No.: US 9,975,064 B2
(45) Date of Patent: May 22, 2018

(54) SYSTEMS AND METHODS FOR UNIPOLAR SEPARATION OF EMULSIONS AND OTHER MIXTURES

(71) Applicant: Massachusetts Institute of Technology, Cambridge, MA (US)

(72) Inventors: Seyed Reza Mahmoudi, Waltham, MA (US); Kripa K. Varanasi, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 113 days.

(21) Appl. No.: 15/220,203

(22) Filed: Jul. 26, 2016

(65) Prior Publication Data

US 2017/0021287 A1    Jan. 26, 2017

Related U.S. Application Data

(63) Continuation of application No. 14/254,863, filed on Apr. 16, 2014, now Pat. No. 9,427,679.

(Continued)

(51) Int. Cl.
*B01D 17/06* (2006.01)
*B01D 17/04* (2006.01)
(Continued)

(52) U.S. Cl.
CPC ......... *B01D 17/045* (2013.01); *B01D 17/047* (2013.01); *B01D 17/06* (2013.01);
(Continued)

(58) Field of Classification Search
CPC .............................. B01D 17/06; B01D 17/045
See application file for complete search history.

(56) References Cited

U.S. PATENT DOCUMENTS 3,016,345 A * 1/1962 Price .................... B01D 17/045
134/10
3,247,091 A    4/1966 Stuetzer
(Continued)

FOREIGN PATENT DOCUMENTS

CN      86105817 A    1/1987
CN      87202063 U    5/1988
(Continued)

OTHER PUBLICATIONS

Allain et al., A New Method for Contact-Angle Measurements of Sessile Drops, Journal of Calloid and Interface Science, vol. 107, No. 1, Sep. 1985, 9 pages.
(Continued)

*Primary Examiner* — Brian W Cohen
(74) *Attorney, Agent, or Firm* — Choate, Hall & Stewart, LLP; William R. Haulbrook; Alexander D. Augst

(57) ABSTRACT

Embodiments discussed herein relate to systems and methods for separating two or more phases of an emulsion or other mixture. The methods include providing the mixture with a net and unipolar charge (e.g., such that adjacent droplets therein acquire net and unipolar charges), thereby enhancing coalescence of like-phase droplets therein and producing, or enhancing the production of, two or more consolidated phases; and collecting the two or more consolidated phases.

16 Claims, 23 Drawing Sheets

Related U.S. Application Data

(60) Provisional application No. 61/812,700, filed on Apr. 16, 2013.

(51) Int. Cl.
| | | |
|---|---|---|
| *B03C 5/02* | (2006.01) | |
| *B03C 11/00* | (2006.01) | |
| *C10G 33/02* | (2006.01) | |
| *C07K 1/14* | (2006.01) | |
| *C12N 13/00* | (2006.01) | |
| *C12N 15/10* | (2006.01) | |

(52) U.S. Cl.
CPC .............. *B03C 5/026* (2013.01); *B03C 11/00* (2013.01); *C07K 1/14* (2013.01); *C10G 33/02* (2013.01); *C12N 13/00* (2013.01); *C12N 15/1003* (2013.01); *B03C 2201/02* (2013.01)

(56) References Cited

U.S. PATENT DOCUMENTS

| | | | |
|---|---|---|---|
| 3,314,872 A * | 4/1967 | Waterman | C10G 33/02 204/563 |
| 4,069,933 A | 1/1978 | Newing | |
| 4,204,021 A | 5/1980 | Becker | |
| 4,316,745 A | 2/1982 | Blount | |
| 4,606,801 A | 8/1986 | Prestridge et al. | |
| 5,624,713 A | 4/1997 | Ramer | |
| 5,853,802 A | 12/1998 | Boyer et al. | |
| 7,622,197 B2 | 11/2009 | Balow et al. | |
| 7,722,951 B2 | 5/2010 | Li et al. | |
| 7,887,934 B2 | 2/2011 | Gentleman et al. | |
| 7,892,660 B2 | 2/2011 | Gentleman et al. | |
| 7,897,271 B2 | 3/2011 | Gentleman et al. | |
| 7,901,798 B2 | 3/2011 | Gentleman et al. | |
| 7,977,267 B2 | 7/2011 | Gentleman et al. | |
| 8,057,922 B2 | 11/2011 | Gentleman et al. | |
| 8,057,923 B2 | 11/2011 | Gentleman et al. | |
| 8,062,775 B2 | 11/2011 | Gentleman et al. | |
| 8,173,279 B2 | 5/2012 | Gentleman et al. | |
| 8,178,219 B2 | 5/2012 | Gentleman et al. | |
| 8,222,172 B2 | 7/2012 | Gentleman et al. | |
| 8,236,432 B2 | 8/2012 | Gentleman et al. | |
| 8,574,704 B2 | 11/2013 | Smith et al. | |
| 2002/0164443 A1 | 11/2002 | Oles et al. | |
| 2003/0096083 A1 | 5/2003 | Morgan et al. | |
| 2003/0134035 A1 | 7/2003 | Lamb et al. | |
| 2003/0203117 A1 | 10/2003 | Bartkowiak et al. | |
| 2004/0026832 A1 | 2/2004 | Gier et al. | |
| 2004/0219373 A1 | 11/2004 | Deruelle et al. | |
| 2005/0003146 A1 | 1/2005 | Spath | |
| 2005/0016489 A1 | 1/2005 | Endicott et al. | |
| 2005/0112326 A1 | 5/2005 | Nun et al. | |
| 2005/0136217 A1 | 6/2005 | Barthlott et al. | |
| 2005/0145576 A1 | 7/2005 | Munson | |
| 2005/0208272 A1 | 9/2005 | Groll | |
| 2006/0013735 A1 | 1/2006 | Engelking et al. | |
| 2006/0078724 A1 | 4/2006 | Bhushan et al. | |
| 2006/0147675 A1 | 7/2006 | Nun et al. | |
| 2006/0204738 A1 | 9/2006 | Dubrow et al. | |
| 2006/0246226 A1 | 11/2006 | Dai et al. | |
| 2007/0031639 A1 | 2/2007 | Hsu et al. | |
| 2007/0207335 A1 | 9/2007 | Karandikar et al. | |
| 2007/0282247 A1 | 12/2007 | Desai et al. | |
| 2007/0298216 A1 | 12/2007 | Jing et al. | |
| 2008/0085070 A1 | 4/2008 | Hirata et al. | |
| 2008/0118763 A1 | 5/2008 | Balow et al. | |
| 2009/0155609 A1 | 6/2009 | Gentleman et al. | |
| 2009/0231273 A1 | 9/2009 | Lashina et al. | |
| 2010/0092621 A1 | 4/2010 | Akutsu et al. | |
| 2010/0285229 A1 | 11/2010 | Elbahri et al. | |
| 2011/0077172 A1 | 3/2011 | Aizenberg et al. | |
| 2011/0201984 A1 | 8/2011 | Dubrow et al. | |
| 2011/0283778 A1 | 11/2011 | Angelescu et al. | |
| 2012/0036846 A1 | 2/2012 | Aizenberg et al. | |
| 2013/0032316 A1 | 2/2013 | Dhiman et al. | |
| 2013/0034695 A1 | 2/2013 | Smith et al. | |
| 2013/0062285 A1 | 3/2013 | Hoek et al. | |
| 2013/0146536 A1 | 6/2013 | Tarabara et al. | |
| 2013/0220813 A1 | 8/2013 | Anand et al. | |
| 2013/0251769 A1 | 9/2013 | Smith et al. | |
| 2013/0251942 A1 | 9/2013 | Azimi et al. | |
| 2013/0251946 A1 | 9/2013 | Azimi et al. | |
| 2013/0251952 A1 | 9/2013 | Smith et al. | |
| 2013/0333789 A1 | 12/2013 | Smith et al. | |
| 2013/0335697 A1 | 12/2013 | Smith et al. | |
| 2013/0337027 A1 | 12/2013 | Smith et al. | |
| 2014/0291420 A1 | 10/2014 | Dhiman et al. | |

FOREIGN PATENT DOCUMENTS

| | | |
|---|---|---|
| CN | 88200107 U | 10/1988 |
| CN | 1675449 A | 9/2005 |
| CN | 100344341 C | 10/2007 |
| CN | 101269960 B | 5/2011 |
| DE | 198 18 956 A1 | 11/1998 |
| JP | 1 170932 A | 7/1989 |
| JP | 5 240251 A | 9/1993 |
| JP | 2004 037764 A | 2/2004 |
| JP | 2008240910 A | 10/2008 |
| TW | I 233 968 B | 6/2005 |
| WO | WO-85/04818 A1 | 11/1985 |
| WO | WO-85/04819 A1 | 11/1985 |
| WO | WO-93/17077 A1 | 9/1993 |
| WO | WO-99/36490 A1 | 7/1999 |
| WO | WO-2002/062568 A2 | 8/2002 |
| WO | WO-2003/071275 A1 | 8/2003 |
| WO | WO-2004/016907 A1 | 2/2004 |
| WO | WO-2006/017009 A2 | 2/2006 |
| WO | WO-2006/091235 A1 | 8/2006 |
| WO | WO-2007/019362 A1 | 2/2007 |
| WO | WO-2008/111603 A1 | 9/2008 |
| WO | WO-2010/082710 A1 | 7/2010 |
| WO | WO-2010/129807 A1 | 11/2010 |
| WO | WO-2011/087458 A1 | 7/2011 |
| WO | WO-2011/143371 A1 | 11/2011 |
| WO | WO-2012/024099 A1 | 2/2012 |
| WO | WO-2012/100099 A2 | 7/2012 |
| WO | WO-2012/100100 A2 | 7/2012 |
| WO | WO-2013/022467 A2 | 2/2013 |
| WO | WO-2013/130118 A1 | 9/2013 |
| WO | WO-2013/141888 A1 | 9/2013 |
| WO | WO-2013/141953 A2 | 9/2013 |

OTHER PUBLICATIONS

Anand et al., Enhanced Condensation on Lubricant-Impregnated Nanotextured Surfaces. ACS Nano, 6(11):10122-10129 (2012).

Antonini et al., Water Drops Dancing on Ice: How Sublimation Leads to Drop Rebound, PRL 111, 014501 (2013).

Arkles, Hydrophobicity, Hydrophilicity and Silanes, Paint and Coatings Industry, Oct. 1, 2006, 10 pages.

Ashkin et al., Optical levitation by radiation pressure. Applied Physics Letters, 19(8):283-285 (1971).

Ashkin et al., Optical levitation of liquid drops by radiation pressure. Science, 187(4181):1073-1075 (1975).

Avedisian et al., Leidenfrost boiling of methanol droplets on hot porous/ceramic surfaces. International Journal of Heat and Mass Transfer, 30(2):379-393 (1987).

Azimi, G. et al., Hydrophobicity of rare-earth oxide ceramics, Nature Materials, DOI:10.1038/NMAT3545, (2013).

Baier et al., Propulsion Mechanisms for Leidenfrost Solids on Ratchet Surfaces. arXiv preprint arXiv:1208.5721 (2012).

Baier et al., Propulsion mechanisms for Leidenfrost solids on ratchets. Physical Review E—Statistical, Nonlinear, and Soft Matter Physics, 87(2) (2013).

Barnes, Geoff T., The Potential for Monolayers to Reduce the Evaporation of Water From Large Water Storages, Agricultural Water Management 95, 4:339-353, (2008).

Bauer et al., The insect-trapping rim of Nepenthes pitchers: surface structure and function, Plant Signaling & Behavior, 4 (11): 1019-1023 (2009).

(56) References Cited

OTHER PUBLICATIONS

Beaugnon et al., Dynamics of magnetically levitated droplets. Physica B: Condensed Matter, 294-295:715-720 (2001).
Biance et al., Leidenfrost drops. Physics of Fluids, 15(6):1632-1637 (2003).
Bico et al., Pearl drops. Europhysics Letters, 47(2):220-226 (1999).
Blossey, R., Self-cleaning surfaces—Virtual realities. Nature Materials, 2(5):301-306 (2003).
Bohn et al., Insect aquaplaning: Nepenthes pitcher plants capture prey with the peristome, a fully wettable water-lubricated anisotropic surface, Proceedings of the National Academy of Sciences,14138-14143 (2004).
Burton, et al., Geometry of the Vapor Layer Under a Leidenfrost Drop. Physical Review Letters, 109(7):074301 (2012).
Cao et al., Anti-Icing Superhydrophobic Coatings, Langmuir Letter, 2009, A-E.
Cassie et al., Wettability of porous surfaces, Transactions of the Faraday Society, 40: 546-551 (1944).
Celestini, et al., Take Off of Small Leidenfrost Droplets. Physical Review Letters, 109(3):034501 (2012).
Chandra et al., Leidenfrost evaporation of liquid nitrogen droplets. Transactions—ASME: Journal of Heat Transfer, 116(4):999-1006 (1994).
Chandra et al., Observations of droplet impingement on a ceramic porous surface. International Journal of Heat and Mass Transfer 35(10):2377-2388 (1992).
Chen et al., A Wettability Switchable Surface by Microscale Surface Morphology Change, Journal of Micromechanics & Microengineering, Institute of Physics Publishing, 17(3): 489-195 (2007).
Cummings et al., Oscillations of magnetically levitated aspherical droplets. Journal of Fluid Mechanics, 224:395-416 (1991).
Deng et al., Nonwetting of impinging droplets on textured surfaces. Applied Physics Letters, 94(13) 133109 1-3 (2009).
Eck, S. et al., Growth and thermal properties of ultrathin cerium oxide layers on Rh(111), Surface Science, 520:173-185, (2002).
Elbahri et al., Anti-lotus effect for nanostructuring at the leidenfrost temperature. Advanced Materials, 19(9):1262-1266 (2007).
Feng et al., Design and creation of superwetting/antiwetting surfaces. Advanced Materials, 18(23):3063-3078 (2006).
Fondecave, R. and Wyart, F.B., Polymers as Dewetting Agents, Marcomolecules 31:9305-9315 (1998).
Fujimoto et al., Deformation and rebounding processes of a water droplet impinging on a flat surface above Leidenfrost temperature. Journal of Fluids Engineering, Transactions of the ASME, 118(1):142-149 (1996).
Furmidge, Studies at Phase Interfaces, Journal of Colloid Science, 1962, 17: 309-324.
Gao et al., Artificial lotus leaf prepared using a 1945 patent and a commercial textile. Langmuir, 22(14):5998-6000 (2006).
Goldshtik et al., A liquid drop on an air cushion as an analogue of Leidenfrost boiling. Journal of Fluid Mechanics, 166:1-20 (1986).
Gradeck et al., Heat transfer for Leidenfrost drops bouncing onto a hot surface. Experimental Thermal and Fluid Science, 47:14-25 (2013).
Hashmi et al., Leidenfrost levitation: Beyond droplets. Scientific Reports, 2:797:1-4 (2012).
Hejazi et al., Wetting Transitions in Two-, Three-, and Four-Phase Systems, Langmuir, 28:2173-2180 (2012).
Holden et al., The Use of Organic Coatings to Promote Dropwise Condensation of Steam, Journal of Heat Transfer, 109: 768-774 (1987).
International Preliminary Report on Patentability, PCT/US2011/061498, dated Feb. 13, 2014, 12 pages.
International Search Report and Written Opinion for PCT/US2011/061498, dated Jul. 31, 2012, 17 pages.
International Search Report for PCT/US2014/034432, dated Aug. 14, 2014, 4 pages.
International Search Report, PCT/US2011/061898, dated Apr. 24, 2013, 6 pages.
International Search Report, PCT/US2012/030370, dated Oct. 15, 2012, 6 pages.
International Search Report, PCT/US2012/042326, dated Dec. 3, 2012, 4 pages.
International Search Report, PCT/US2012/042327, dated May 16, 2013, 6 pages.
International Search Report, PCT/US2013/021558, dated Oct. 11, 2013, 5 pages.
International Search Report, PCT/US2013/028439, dated Dec. 5, 2013, 6 pages.
International Search Report, PCT/US2013/042771, dated May 26, 2014, 4 pages.
International Search Report, PCT/US2013/045731, dated Nov. 12, 2013, 3 pages.
International Search Report, PCT/US2013/070827, dated Mar. 27, 2014, 7 pages.
Iwasa, et al., 'Electromaglev'—Magnetic levitation of a superconducting disc with a DC field generated by electromagnets: Part 1. Theoretical and experimental results on operating modes, lift-to-weight ratio, and suspension stiffness. Cryogenics, 37(12):807-816, (1997).
Jung et al., Are Superhydrophobic Surfaces Best for Icephobicity? Langmuir, 27(6):3059-3066 (2011).
Kim et al., Hierarchical or not? Effect of the length scale and hierarchy of the surface roughness on omniphobicity of lubricant-infused substrates. Nano Letters, 13(4):1793-1799 (2013).
Kim et al., Levitation Time Measurement of Water Drops on the Surface of Liquid Nitrogen, Journal of the Korean Physical Society, vol. 58, No. 6, pp. 1628-1632 (Jun. 2011).
Kim, Heetae, Floating Phenomenon of a Water Drop on the Surface of Liquid Nitrogen, Journal of the Korean Physical Society, vol. 49, No. 4, pp. L1335-L1338 (Oct. 2006).
Kulinich et al., Ice Adhesion on Super-Hydrophobic Surfaces, Applied Surface Science, 2009, 225: 8153-8157.
Lafuma, A. et al., Slippery Pre-Suffused Surfaces; EPL, 96: 56001-p. 1-56001-p. 4 (2011).
Lagubeau et al., Leidenfrost on a ratchet. Nature Physics, 7(5):395-398 (2011).
Lee et al., Dynamic Wetting and Spreading Characteristics of a Liquid Droplet Impinging on Hydrophobic Textured Surfaces, Langmuir, (2011), 27, 6565-6573.
Leidenfrost, J. G., On the fixation of water in diverse fire. International Journal of Heat and Mass Transfer, 9(11):1153-1166 (1966).
Li et al., Dynamic Behavior of the Water Droplet Impact on a Textured Hydrophobic/Superhydrophobic Surface: The Effect of the Remaining Liquid Film Arising on the Pillars' Tops on the Contact Time, Langmuir, (2010), 26(7), 4831-4838.
Linke et al., Self-propelled leidenfrost droplets. Physical Review Letters, 96(15) (2006).
Liu et al., Metallic Surfaces with Special Wettability, Nanoscale, 3:825-238 (2011).
Marin et al., Capillary droplets on Leidenfrost micro-ratchets. arXiv preprint arXiv:1210.4978 (2012).
Matolín, V. et al., Growth of ultra-thin cerium oxide layers on Cu(111), Surface Science 254:153-155, (2007).
Meuler et al., Exploiting Topographical Texture to Impact Icephobicity, ACS Nano, 2010, 4(12): 7048-7052.
Mills, A. A., Pillow lavas and the Leidenfrost effect. Journal of the Geological Society, 141(1):183-186 (1984).
Mishchenko et al., Design of ice-free nanostructured surfaces based on repulsion of impacting water droplets. ACS Nano, 4(12):7699-7707 (2010).
Mullins, D. R. et al., Ordered cerium oxide thin films gown on Ru(0001) and Ni(111), Surface Science, 429:186-198, (1999).
Onda et al., Super-water-repellent fractal surfaces. Langmuir, 12(9) (1996).
Ou et al., Laminar drag reduction in microchannels using ultrahydrophobic surfaces. Physics of Fluids, 16(12):4635-4643 (2004).
Park et al., A Numerical Study of the Effects of Superhydrophobic Surface on Skin-Friction Drag in Turbulent Channel Flow, Phys. Fluids 25, 110815 (2013).

(56) References Cited

OTHER PUBLICATIONS

Piroird et al., Magnetic control of Leidenfrost drops. Physical Review E—Statistical, Nonlinear, and Soft Matter Physics, 85(5) (2012).
Pozzato et al., Superhydrophobic surfaces fabricated by nanoimprint lithography, Microelectronic Engineering, 83, (2006), 884-888.
Prat et al., On the effect of surface roughness on the vapor flow under Leidenfrost-Levitated droplets. Journal of Fluids Engineering, Transactions of the ASME, 117(3):519-525 (1995).
Quéré et al., Surfing the hot spot. Nature Materials, 5(6):429-430 (2006).
Quéré, D., Leidenfrost dynamics, Annu. Rev. Fluid Mech., 197-215 (2013).
Quéré, D., Non-sticking drops, Institute of Physics Publishing, Rep.Prog.Phys., 68(11):2495-2532 (2005).
Rausch et al., On the Characteristics of Ion Implanted Metallic Surfaces Inducing Dropwise Condensation of Steam, Langmuir, 26(8): 5971-5975 (2010).
Reyssat et al., Dynamical superhydrophobicity. Faraday Discussions, 146:19-33 (2010).
Reyssat, et al., Bouncing transitions on microtextured materials. Europhysics Letters, 74(2):306-312 (2006).
Richard, D. et al., Contact time of a bouncing drop, Nature 417:(6891):811 (2002).
Roosen et al., Optical levitation by means of two horizontal laser beams: a theoretical and experimental study. Physics Letters A, 59(1):6-8 (1976).
Rothstein, J. P., Slip on superhydrophobic surfaces, ANRV400-FL42-05, ARI, 89-109 (2010).
Rykaczewski et al., Mechanism of Frost Formation of Lubricant-Impregnated Surfaces, Langmuir 2013, 29 5230-5238, 13 pages.
Schierbaum, Klaus-Dieter, Ordered ultra-thin cerium oxide overlayers on Pt(111) single crystal surfaces studied by LEED and XPS, Surface Science, 399:29-38, (1998).
Seiwert et al., Coating of a Textured Solid, J. Fluid Mech., 2011, 669: 55-63.
Sekeroglu et al., Transport of a soft cargo on a nanoscale ratchet. Applied Physics Letters, 99(6) (2011).
Smith et al., Droplet Mobility on Lubricant-Impregnated Surfaces, Soft Matter, 2012(9): 1772-1780 (2012).
Smith et al., Liquid-encapsulating surfaces: overcoming the limitations of superhydrophobic surfaces for robust non-wetting and anti-icing surfaces. In Bulletin of the American Physical Society (2011) Abstract Only.
Snoeijer et al., Maximum size of drops levitated by an air cushion. Physical Review E—Statistical, Nonlinear, and Soft Matter Physics, 79(3) (2009).
Song et al., Superhydrophobic Surfaces Produced by Applying a Self-Assembled Monolayer to Silicon Micro/Nano-Textured Surfaces, Nano Research, 2009, 2: 143-150.
Song et al., Vitrification and levitation of a liquid droplet on liquid nitrogen, PNAS Early Edition, pp. 1-5 (2010).
Sutara, F. et al., Epitaxial growth of continuous $CeO_2$(111) ultra-thin films on Cu(111), Thin Solid Films, 516:6120-6124 (2008).
Trinh et al., The dynamics of ultrasonically levitated drops in an electric field. Physics of Fluids, 8(1):43-61 (1996).
Tuteja et al., Designing superoleophobic surfaces. Science, 318(5856):1618-1622 (2007).
Tuteja et al., Robust omniphobic surfaces. Proceedings of the National Academy of Sciences of the United States of America, 105(47):18200-18205 (2008).
U.S. Non-Final Office Action, U.S. Appl. No. 13/902,689, dated Sep. 22, 2014, 12 pages.
Vakarelski et al., Drag reduction by leidenfrost vapor layers. Physical Review Letters, 106(21) (2011).
Vakarelski et al., Stabilization of Leidenfrost vapour layer by textured superhydrophobic surfaces. Nature, 489(7415):274-277 (2012).
Varanasi et al., Frost formation and ice adhesion on superhydrophobic surfaces. Applied Physics Letters, 97(23) (2010).
Varanasi et al., Spatial Control in the Heterogeneous Nucleation of Water, Applied Physics Letters, 95: 094101-01-03 (2009).
Weber et al., Aero-acoustic levitation: A method for containerless liquid-phase processing at high temperatures. Review of Scientific Instruments, 65(2):456-465 (1994).
Weickgenannt et al., Inverse-Leidenfrost phenomenon on nanofiber mats on hot surfaces. Physical Review E—Statistical, Nonlinear, and Soft Matter Physics, 84(3) (2011).
Weilert et al., Magnetic levitation and noncoalescence of liquid helium. Physical Review Letters, 77(23):4840-4843 (1996).
Welter et al., Acoustically levitated droplets—A new tool for micro and trace analysis. Fresenius' Journal of Analytical Chemistry, 357(3):345-350 (1997).
Wenzel, Resistance of Solid Surfaces to Wetting by Water, Industrial & Engineering Chemistry, 28(8): 988-994 (1936).
Wong et al., Bioinspired Self-Repairing Slippery Surfaces with Pressure-Stable Omniphobicity, Nature, 477(7365):443-447 (2011).
Written Opinion for PCT/US2014/034432, dated Aug. 14, 2014, 8 pages.
Written Opinion, PCT/US2011/061898, dated Apr. 24, 2013, 9 pages.
Written Opinion, PCT/US2012/030370, dated Oct. 15, 2012, 10 pages.
Written Opinion, PCT/US2012/042326, dated Dec. 3, 2012, 7 pages.
Written Opinion, PCT/US2012/042327, dated May 16, 2013, 6 pages.
Written Opinion, PCT/US2013/021558, dated Oct. 11, 2013, 7 pages.
Written Opinion, PCT/US2013/028439, dated Dec. 5, 2013, 11 pages.
Written Opinion, PCT/US2013/042771, dated May 26, 2014, 7 pages.
Written Opinion, PCT/US2013/045731, dated Nov. 12, 2013, 3 pages.
Written Opinion, PCT/US2013/070827, dated Mar. 27, 2014, 15 pages.
Würger, A., Leidenfrost gas ratchets driven by thermal creep. Physical Review Letters, 107(16) (2011).
Yarin et al., On the acoustic levitation of droplets. Journal of Fluid Mechanics, 356:65-91 (1998).
Yasuda et al., Levitation of metallic melt by using the simultaneous imposition of the alternating and the static magnetic fields. Journal of Crystal Growth, 260(3-4):475-485 (2004).
Yu et al., Containerless solidification of oxide material using an electrostatic levitation furnace in microgravity. Journal of Crystal Growth, 231(4):568-576 (2001).
Zhao et al., Dropwise condensation of Steam on Ion Implanted Condenser Surfaces, Heat Recovery Systems & CHP, 14(5): 525-534 (1994).

\* cited by examiner

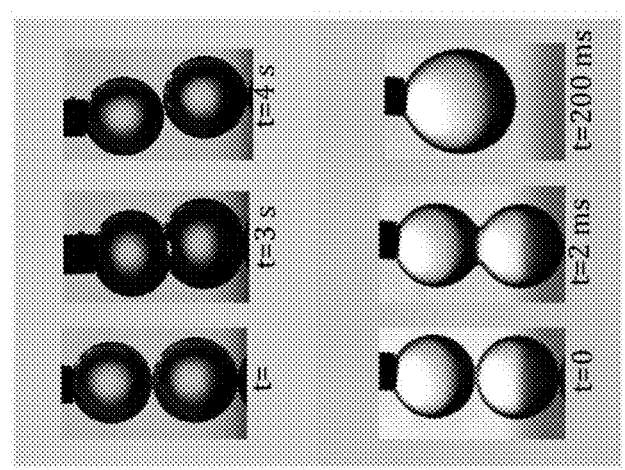
FIG. 6B
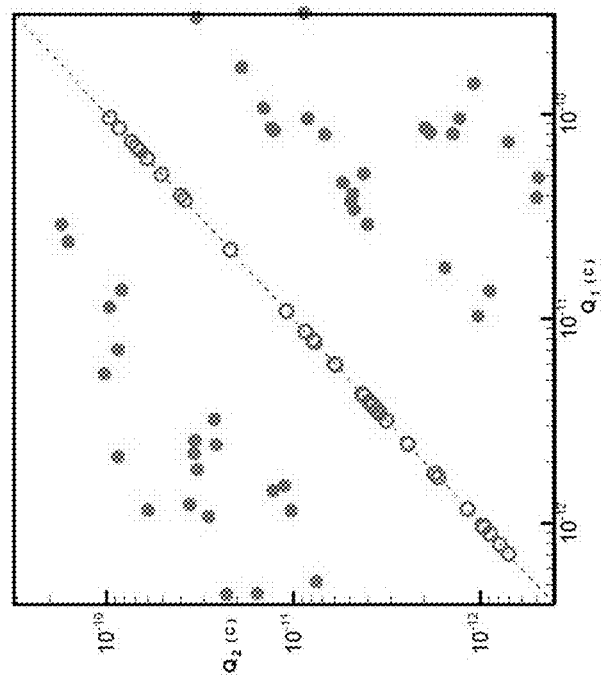
FIG. 6A
FIG. 6C

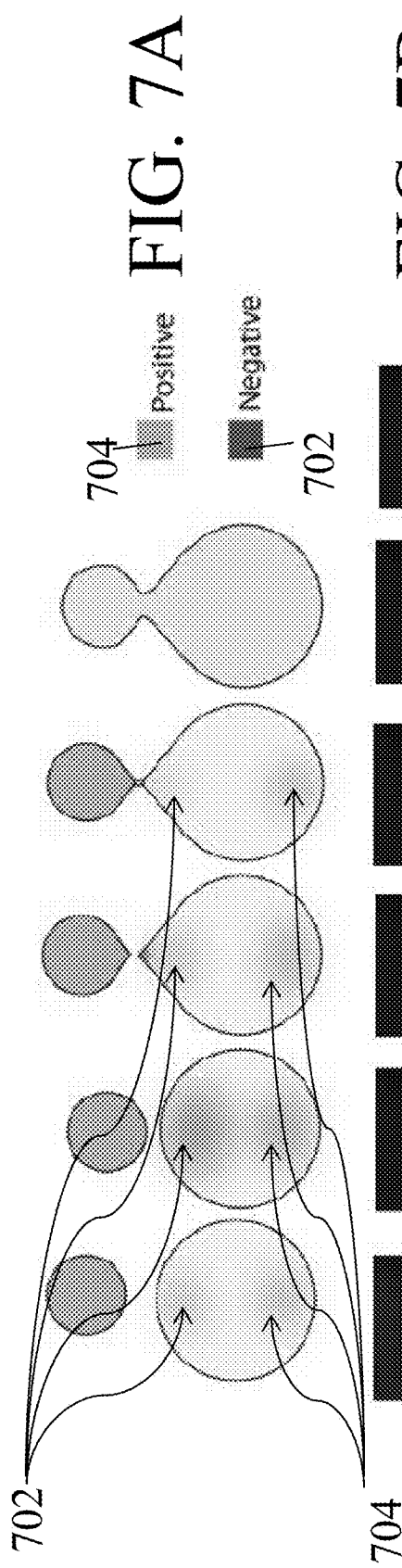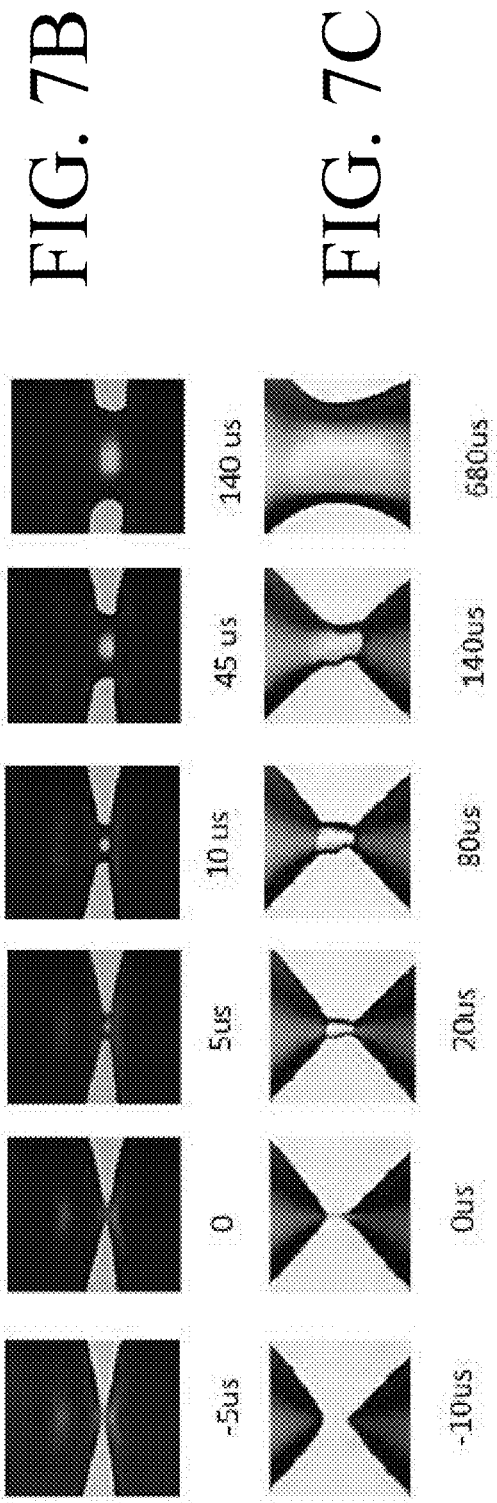
FIG. 7A  FIG. 7B  FIG. 7C

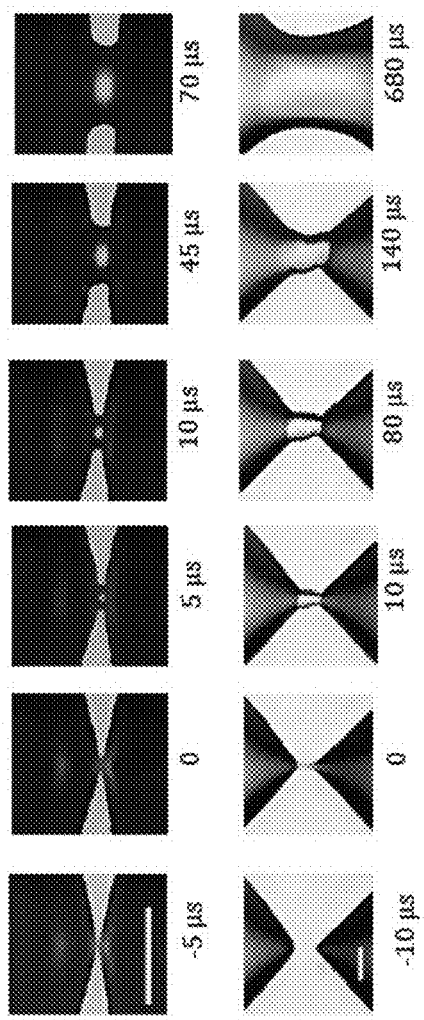
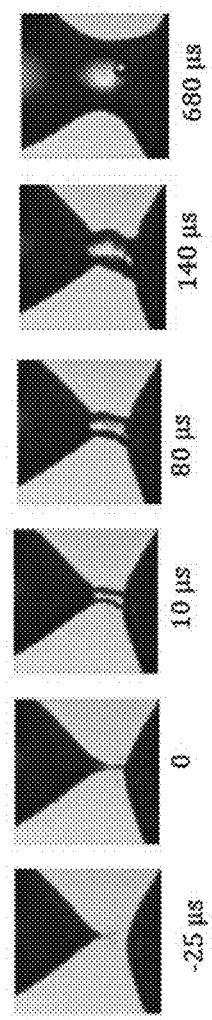
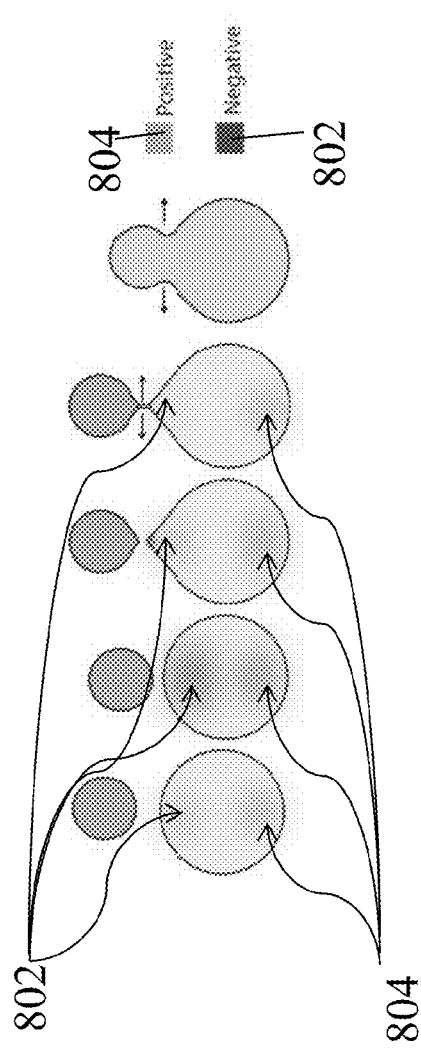
FIG. 8A
FIG. 8B
FIG. 8C
FIG. 8D

Corona discharge for two drops in bulk oil

Corona discharge for 10% water in 90% oil

Triboelectrification of PMMA substrate rubbed with polyester fiber 0.083 μC/m²

40 μm

SYSTEMS AND METHODS FOR UNIPOLAR SEPARATION OF EMULSIONS AND OTHER MIXTURES

CROSS REFERENCE TO RELATED APPLICATIONS

This application is a Continuation application of U.S. patent application Ser. No. 14/254,863, filed Apr. 16, 2014, which claims priority to and the benefit of U.S. Provisional Patent Application 61/812,700, filed Apr. 16, 2013, titled "Systems and Methods for Unipolar Emulsion Separation", the entire contents of each of which are hereby incorporated by reference in their entireties.

FIELD OF INVENTION

This invention relates generally to separation of two or more phases of an emulsion or other mixture. In certain embodiments, the invention relates to separation of liquid phases in an emulsion or other mixture by coalescing like-charged droplets.

BACKGROUND OF THE INVENTION

Emulsions appear in a wide range of industries, for example, petrochemical processing, food processing, metal finishing and polishing, textile, paper, cosmetic, pharmaceutical, biotechnology, as well as other industries. It is often necessary to perform separations of one or more components of these emulsions, for example, separation of an aqueous liquid phase (e.g., water) from a non-aqueous liquid phase (e.g., oil) in an emulsion that is composed of either predominately aqueous phase or predominately non-aqueous phase.

For example, in petroleum industries, water is considered a contaminant of the oil products and must be separated from the oil product before further processing, because water may cause considerable corrosion of the processing equipment and may affect the life of the equipment, which may negatively impact the entire plant. Even trace amounts of water in the oil may cause serious problems further down the line. In a contrasting example, oils are a common pollutant in downstream wastewater and byproducts produced in the food and metal industries and should be separated from the wastewater. Separating oil from water (including trace amounts of oil) is a significant challenge. In order to be released back into environment, government regulations require that the oil does not contain more than certain amounts of oil in the water. The maximum allowed quantity of oil for may be 10 ppm of oil or less.

A significant challenge is to reduce the capital costs of energy consumption and reduce or eliminate the use of chemical additives (especially those additives that are considered pollutants and/or additives that otherwise have a negative environmental effect), which are the traditional method of promoting the breakup of emulsions and other mixtures into their components. Another significant challenge is achieving desired levels of separation of oil and water.

There are a number of traditional methods for separating components of emulsions. One of the most common separation techniques is gravity separation. As a primary and low cost treatment step, gravity separation is typically used for separation of emulsions with larger droplet sizes. Gravity separation may be accompanied by a sedimentation process. For example, oil may adhere to the surface of solid particles and be effectively removed by sedimentation. However, gravity separation is not effective for destabilization of emulsions with small droplet sizes, because the time of sedimentation is impractically long (the required time is roughly inversely proportional to the droplet size squared).

In order to separate emulsions with fine droplets, emulsions are typically pretreated chemically to promote coagulation and increase floc size, thereby destabilizing the emulsified phase during gravity separation. In some conventional methods, the emulsion may also be heated to reduce the viscosity, induce stronger density difference, and reduce the surface tension of the stabilizing films between droplets. Other chemical treatment methods increase the acidity or add ionic agents to the emulsion to neutralize the charge of droplets. Chemical treatment methods are energy intensive and may introduce several undesired chemical contaminants. Separation of the additional chemical contaminant may require post-processing unit operations for separation of chemicals, resulting in increased cost and greater risk of environmental pollution.

In addition to gravity separation, other physical methods for destabilizing emulsions include heating, centrifugation, filtration, ultrafiltration (e.g., using membranes), and reverse osmosis. Ultrafiltration (e.g., membrane ultrafiltration) has a smaller chemical footprint than gravity separations and can be somewhat effective for emulsions with small droplet sizes (e.g., smaller than 100 μm). However, the costs associated with ultrafiltration tend to be high (or prohibitive) due to high energy consumption required for ultrafiltration of large volumes, and due to degeneration of the membrane coating materials over time (e.g., such that new membranes need to be provided on a regular basis, further increasing the costs).

Another physical method for separating components of emulsions is electrostatic separation. There are three electrostatic body forces that can be used to induce coalescence. The electric body force in a dielectric liquid, that results from an imposed electric field, can be expressed as:

$$\vec{f} = \rho_c \vec{E} - \frac{1}{2}\vec{E}^2 \nabla \varepsilon + \frac{1}{2} \nabla \left[\vec{E}^2 \rho \left(\frac{\partial \varepsilon}{\partial \rho}\right)_T\right] \quad (1)$$

where $\rho_c$ is volume charge density, $\varepsilon$ is the fluid permittivity, p is the fluid density, and T is the fluid temperature. The first term on the right hand side of Eq. (1) is the electrophoretic, or Coulombic, force that results from the net free space charges in the fluid. The second term, known as the dielectrophoretic force, arises from the permittivity gradient. The last term, called the electrostrictive force, is important only for compressible fluids.

In these electrostatic separators, it is primarily the second term, dielectrophoretic force, which is exploited to promote the coalescence of droplets in the emulsion. In one conventional technique, two parallel plates are immersed in the emulsion with a small gap spacing between the electrodes. These immersed electrodes are used to induce an external electric field to the bulk of the emulsion. The water droplets in the medium become polarized and positive-negative ends attract each other so that the oil film between two droplets squeezes and is drained. The two adjacent drops may merge together when the layer of the oil between them is ruptured. These droplets do not acquire a net charge. One limitation of this technique is that the polarization force is scaled with the size of droplet. The smaller the droplet size, the larger the field that must be applied. Moreover, the orientation of two adjacent droplets is important. If the angle is not appropriate, two droplets repel rather attract and they cannot be merged—this is a significant limitation of conventional electrostatic separators. The electrohydrodynamic-induced flow and bi-polar attraction (positive-negative attraction) caused by the applied electrophoretic force may induce coalescence of droplets.

The electrohydrodynamic flow generated by interactions of the electric field and fluid flow may also increase the chance of droplet coalescence. AC and DC fields have been used to establish homogeneous or nonhomogeneous fields between the immersed electrodes. Electrostatic separators may be effective in separating droplets as small as a few hundred microns; however, these separators are not effective for smaller droplet sizes in moderate electrical fields.

Although electrostatic separators show some promise, they also suffer from several significant limitations. In conventional electrocoalescencers, both electrodes are immersed in the emulsions. The immediate consequence is that the technique cannot be reliably used when the content of water in the emulsion is high, for example, greater than 40 wt. %. The high content of water may limit the level of applied potential to the electrodes so that even moderate fields may cause electrostatic breakdown. Even when the content of water is moderate or low, the separated water droplets tend to align themselves in the direction of the imposed field and form a chain-like structure across the gap between the electrodes. The formation of this chain may increase the chance of electrostatic discharge and arc across the gap. The electrostatic discharge poses a risk of explosion, as well as corrosion of the electrode or electrode coatings, and increased contamination due to chemical decomposition of oil around the electrodes. Moreover, the electrostatic discharge/breakdown may reduce the rate of coalescence by suppressing the strength of the background electric field, the rate of charging the droplets, and the efficiency of the separator. Additionally, traditional electrostatic separators fail where the aqueous phase has high salt content.

A separation method is needed that is cost-effective, works for emulsions having small droplet size, works irrespective of the salt concentration of the aqueous phase, and does not pose a risk of explosion or require addition of chemical additives to the emulsion.

SUMMARY OF THE INVENTION

Various embodiments of the invention relate to methods and systems for separating two or more phases of an emulsion or other mixture. In certain embodiments, the invention introduces a net and unipolar charge into the mixture such that adjacent droplets therein acquire net and unipolar charges and, surprisingly, enhance coalescence of like-phase droplets, thereby destabilizing the mixture and producing, or enhancing production of, two or more consolidated liquid phases.

Some embodiments discussed herein provide successful separation of two or more phases of an emulsion or other mixture despite high conductivity of a dispersed phase, despite high salt content, and/or despite the presence of a surfactant or other emulsifier. In some embodiments, the conductivity of the mixture is between 1 mS/m to 1 S/m or as high as 10 S/m. The systems and methods described herein are applicable to a wide variety of electrical conductivity ranges. Certain embodiments described herein can separate a variety of mixtures having wide ranges of salt and/or surfactant content without any special adjustment in configuration of electrodes or other invasive manipulation.

In one aspect, the invention provides a method for separating two or more phases of a mixture (e.g., an emulsion), the method including the steps: (a) providing the mixture with a net and unipolar charge (e.g., such that adjacent droplets therein acquire net and unipolar charges), thereby enhancing coalescence of like-phase droplets therein and producing, or enhancing the production of, two or more consolidated phases; and (b) collecting the two or more consolidated phases.

In certain embodiments, step (a) includes bombarding the mixture with ions via corona discharge.

In certain embodiments, step (a) includes providing an emitter electrode (e.g., sharp electrode) and a collector electrode, wherein at least the collector electrode (e.g., blunt electrode) is in physical contact with the mixture and a potential difference is applied between the emitter electrode and the collector electrode at or above a corona discharge threshold.

In certain embodiments, the emitter electrode is not in physical contact with the mixture.

In certain embodiments, a gaseous medium (e.g., nitrogen, oxygen, air, argon, helium, etc., or any mixture of different gases) is located between the emitter electrode and the mixture. In some embodiments, the gaseous mixture is stationary. In some embodiments, the gaseous mixture is flowing. In some embodiments, the gaseous flow reduces the corrosion of the electrodes because the by-product of the corona discharge becomes less concentrated. In turn, this significantly reduces the maintenance that needs to be performed for the systems and methods discussed herein. In addition, this increases the useful life of the systems and decreases operation costs. The gaseous medium may be at any temperature and pressure.

In some embodiments, ionized gas may be introduced into the mixture. Collapsing bubbles causes ionization of the gas inside the bubbles.

In certain embodiments, the collector electrode is grounded. In some embodiments, the collector electrode is biased with the same polarity above the ground level. In some embodiments, the emitter electrode energy is at +15 kV, the collector electrode may be ground (0 kV) or the collector electrode can be biased by, e.g., +1 kV.

In certain embodiments, the emitter electrode is a sharp electrode (e.g., a needle, multiple needles, a blade or blades, a thin wire or multiple wires, etc.).

In certain embodiments, the emitter electrode is coated and/or textured (e.g., coated and/or textured with microstructures, nanotubes (e.g., CNT), nano-structures, or other sharp geometries).

In certain embodiments, the emitter electrode is made of or coated with a material resistant to ionization-induced corrosion.

In certain embodiments, the collector electrode includes one or more members selected from the group consisting of a metal, silicon, and a silicon with native oxide, and/or wherein the collector electrode is coated with a dielectric film (e.g., and/or wherein the collector electrode is a substrate that contains the mixture, e.g., is a channel, pipe, plate, etc.). In some embodiments, the collector electrode is not coated with a dielectric film, e.g., in some embodiments, the collector electrode is bare.

In some embodiments, the potential difference between the mixture and the emitter electrode is established by applying high voltage to the needle or by applying high voltage to the mixture by reversing the emitter electrode polarity. In some embodiments, the emitter electrode is a single electrode (e.g., sharp needle, wire, or engineered surface, or any combination thereof).

In some embodiments, an electric field is applied to the mixture via continuous AC or DC discharge or via pulsed discharge. In some embodiments, the discharge is two-phase, three phase, or a multi-phase discharge with a time-lag discharge. In some embodiments, the discharge is a direct discharge or a barrier discharge.

In some embodiments, the applied voltage is adjusted based on properties of the mixture (e.g., chemical properties, physical properties).

In some embodiments, the mixture is separated during transport (e.g., transport on a conveyor belt or another conduit).

In some embodiments, step (a) includes providing a portion of the mixture with a unipolar charge, the method further comprising mixing the charged portion of the mixture into the remaining portion of the mixture, thereby enhancing coalescence of like-phase droplets therein and producing, or enhancing the production of, two or more consolidated phases; and (b) collecting the two or more consolidated phases.

In certain embodiments, step (a) includes injecting, spraying, or otherwise introducing a substance (e.g., liquid droplets, a liquid bath, or a liquid stream) having a net and unipolar charge into the mixture, thereby enhancing coalescence of like-phase droplets therein and producing, or enhancing the production of, the two or more consolidated phases.

In some embodiments, the charge is applied to the mixture directly. In some embodiments, the charge is applied to the mixture indirectly. In some embodiments, step (a) includes injecting an ionized gas having a net and unipolar charge (e.g., ionized in a separate process, ionized during transport to the mixture, ionized via corona discharge in a corona discharge chamber) into the mixture. In some embodiments, the ionized gas passes through the mixture. In some embodiments, the size of the gas bubbles may be decreased to increase the interface of ionized gas bubbles with the mixture. In some embodiments, the ionized gas is injected from a single location into the mixture or from multiple points into the mixture.

In some embodiments, the gas bubbles are injected into the mixture from the top (e.g., from above the mixture). In some embodiments, the gas bubbles are injected into the mixture from the bottom (e.g., from underneath the mixture).

In certain embodiments, step (a) includes introducing the mixture to a substrate having a net and unipolar charge (e.g., a substrate with a charge applied via tribo-electrification).

In certain embodiments, the unipolar charge is positive.
In certain embodiments, the unipolar charge is negative.
In certain embodiments, the mixture, while maintaining a net and unipolar charge, includes a combination of species having positive and negative charges (e.g., which may change over a given time period).

In some embodiments, step (a) includes applying a charge via tribo-electrification during transport of the mixture via a conduit, the conduit comprising a coating configured to improve tribo-electrification charging. In some embodiments, wherein step (a) includes applying a charge by direct injection, conduction, induction of net and unipolar charge, and/or any combination thereof.

In certain embodiments, the mixture includes a plurality of liquid phases.

In certain embodiments, the mixture includes one or more members selected from the group consisting of particles, proteins, DNA, RNA, and cells (e.g., wherein the mixture includes a stabilizing agent such as particles or surfactant).

In certain embodiments, the mixture includes a liquid with low electrical conductivity (e.g., an insulating liquid or a dielectric liquid, e.g., wherein the low conductivity liquid makes up at least 50 wt. % of the mixture). In certain embodiments, the mixture includes a liquid with high electrical conductivity.

In certain embodiments, the mixture includes an aqueous phase, and the aqueous phase has a salt content of at least about 0.5M (e.g., at least about 1M, at least about 1.5M, or at least about 2.0M).

In certain embodiments, prior to introduction of the net and unipolar charge, the mixture includes a phase of droplets having average droplet diameter less than or equal to about 1000 micrometers in diameter (e.g., ≤500 µm, ≤400 µm, ≤300 µm, ≤100 µm, ≤50 µm, ≤30 µm, ≤20 µm, ≤10 µm, ≤1 µm, ≤900 nm, ≤500 nm, ≤300 nm, ≤100 nm, ≤50 nm, ≤30 nm, or ≤10 nm), and wherein the droplets coalesce after introduction of the net and unipolar charge.

In certain embodiments, the mixture is a two-phase emulsion including an aqueous phase and a non-aqueous phase (e.g., oil), wherein the aqueous phase makes up less than or equal to 50 wt. % of the emulsion (e.g., ≤40 wt. %, ≤30 wt. %, ≤20 wt. %, ≤10 wt. %, ≤5 wt. %, ≤3 wt. %, ≤1 wt. %, or ≤0.5 wt. %).

In certain embodiments, the mixture is a two-phase emulsion including an aqueous phase and a non-aqueous phase (e.g., oil), wherein the non-aqueous phase is less than or equal to 50 wt. % of the emulsion (e.g., ≤40 wt. %, ≤30 wt. %, ≤20 wt. %, ≤10 wt. %, ≤5 wt. %, ≤3 wt. %, ≤1 wt. %, or ≤0.5 wt. %).

In some embodiments, the mixture is a three-phase mixture. In some embodiments, the mixture includes a liquid phase, a solid phase, and a gas phase. In some embodiments, the mixture is a bubble-in-oil mixture or a foam-in-oil mixture. In some embodiments, the mixture includes an emulsifier (e.g., a surfactant). In some embodiments, the mixture includes at least one phase having a salt content at least about 0.5M (e.g., at least about 1M, at least about 1.5M, or at least about 2.0M). In some embodiments, the mixture includes a liquid with high electrical conductivity. In some embodiments, the mixture includes an oil, the oil having an electrical conductivity between about $10^{-14}$ S/m (highly insulating) to about $10^{-5}$ S/m (highly conducting). In some embodiments, the mixture has an electrical conductivity between about $10^{-7}$ S/m to about 100 S/m.

In some embodiments, the gas pressure and/or the gas temperature is controlled/modulated to optimize the quality of the discharge (V-I) characteristics and the breakdown limit (e.g., to increase the electrical breakdown limit). In some embodiments, the gas pressure and/or the gas temperature is controlled/modulated to optimize the separation of the mixture (e.g., separation of different phases of an emulsion). In some embodiments, the composition of the gas mixture may be adjusted to control the V-I characteristics and the breakdown limit. In some embodiments, the gas pressure and/or the gas temperature is controlled/modulated to optimize the quality of the discharge (V-I) characteristics and the breakdown limit (e.g., to increase the electrical breakdown limit) based on sea elevation of a location where the separating of the two or more phases takes place.

In another aspect, the invention is directed to a system for separating two or more phases of a mixture (e.g., an emulsion), the system including: (a) a container or support for containing or supporting the mixture therein or thereupon, wherein the container or support includes (e.g., is) a grounded collector electrode, and wherein the container or support includes a ramp, lip, edge, and/or other elevated portion; (b) an emitter electrode not in physical contact with the mixture; and (c) a power source configured to apply a potential difference between the emitter electrode and the collector electrode at or above a corona discharge threshold, wherein a gaseous medium (e.g., nitrogen, oxygen, air, argon, helium, etc., or any combination/mixture thereof) is located between the emitter electrode and the mixture, and wherein the container or support is configured to permit passage of a first phase of the mixture therethrough and/or thereover while disallowing passage of at least a second phase of the mixture therethrough and/or thereover upon application of the potential difference between the emitter electrode and the collector electrode at or above the corona discharge threshold (e.g., taking advantage of the differential spreading or pumping effect of corona discharge separation), thereby causing or promoting separation of two or more phases of the mixture.

In some embodiments, the electrode (emitter and/or collector) discussed herein are bare. In some embodiments, the electrodes (emitter and/or collector) discussed herein are coated.

In certain embodiments, the power source is a conventional power source (e.g., a battery, DC power supply, AC power supply, or AC/DC supply. In certain embodiments, the power source is an electrostatic generator (e.g., a Van de Graaf generator).

In some embodiments, the system is a skimmer, a gravitation separator, or a centrifugal separator. In some embodiments, the system is a skimmer that has been retrofitted to carry out the separation of the mixture. In some embodiments, like-charge induced separation can accelerate the separation process when the mixture is stored in a container.

In some embodiments, the temperature and/or pressure of the gaseous medium is controlled/modulated, based on sea level elevation of the system, to optimize the quality of the discharge (V-I) characteristics and the breakdown limit (e.g., to increase the electrical breakdown limit).

In various embodiments, features described with respect to the methods above can be applied to the system as well.

The methods and/or systems can perform a pre-treatment step in an existing system (e.g., a retrofit of a gravitational and/or sedimentation mixture separation process), or they can be combined with other techniques. For example, in some embodiments, methods and systems described herein may promote coalescence between small droplets to form larger droplets, which are then more easily handled by traditional separation systems (e.g., gravitational, sedimentation, and/or chemical additive separation processes).

Elements of embodiments described with respect to a given aspect of the invention may be used in various embodiments of another aspect of the invention. For example, it is contemplated that features of dependent claims depending from one independent claim can be used in apparatus and/or methods of any of the other independent claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

FIG. 6A is a graph illustrating coalescence and non-coalescence behavior of a pair of water droplets carrying different charge magnitudes in oil, in accordance with some embodiments of the invention. The diameters of droplets were 1 mm. The separation between droplets was 50 µm. Filled circles denote coalescence and open (unfilled) circles represent non-coalescence of droplets.

FIG. 6B illustrates non-coalescence of like-charge water droplets, in accordance with some embodiments of the invention. Droplets were electrically connected and positively charged. Non-coalescence behavior is due to the electrostatic repulsion between equally charged water droplets.

FIG. 6C illustrates coalescence behavior of positively charged water droplets in oil, in accordance with some embodiments of the invention.

FIGS. 7A, 7B and 7C shows a mechanism that occurs upon coalescence of two like-charged droplets in an emulsion, in accordance with some embodiments of the invention. As shown in FIG. 7C, at t=20 microseconds, an electrostatic bridge appears and appears to thicken into a capillary bridge, resulting in coalescence of the droplets.

FIG. 7A illustrates a schematic for a mechanism of like-charge coalescence of droplets, in accordance with some embodiments of the invention. Circles correspond to adjacent droplets. Areas 702 correspond to negative charge densities. Areas 704 correspond to positive charge density areas.

FIG. 8A, FIG. 8B, FIG. 8C, and FIG. 8D, illustrate high speed imaging of interactions for positively charged droplets in oil for relatively small and large initial separations, in accordance with some embodiments of the invention. A mechanism of like-charge coalescence is presented, in accordance with some embodiments of the invention.

FIG. 8A illustrates like-charge droplet coalescence after contact at t=0, in accordance with some embodiments of the invention. Amounts of charges on top and bottom droplets were +35.4 pC and +0.29 pC, respectively. The initial separation of droplets was 50 µm. The scale bar is 0.1 mm in length.

FIG. 8B illustrates like-charge droplet coalescence after contact at t=0, in accordance with some embodiments of the invention. Amounts of charges on top and bottom droplets were +150 pC and +0.18 pC, respectively. The initial separation of droplets was 320 µm. The scale bar is 0.1 mm in length.

FIG. 8C illustrates like-charge droplet coalescence after contact at t=0, in accordance with some embodiments of the invention. Amounts of charges on top and bottom droplets were +310 pC and +0.27 pC, respectively. The initial separation of droplets was 415 µm.

FIG. 8D illustrates a schematic for a mechanism of like-charge coalescence of droplets, in accordance with some embodiments of the invention. Circles correspond to adjacent droplets. Areas 802 correspond to negative charge densities. Areas 804 correspond to positive charge density areas.

DESCRIPTION

Figure 1:
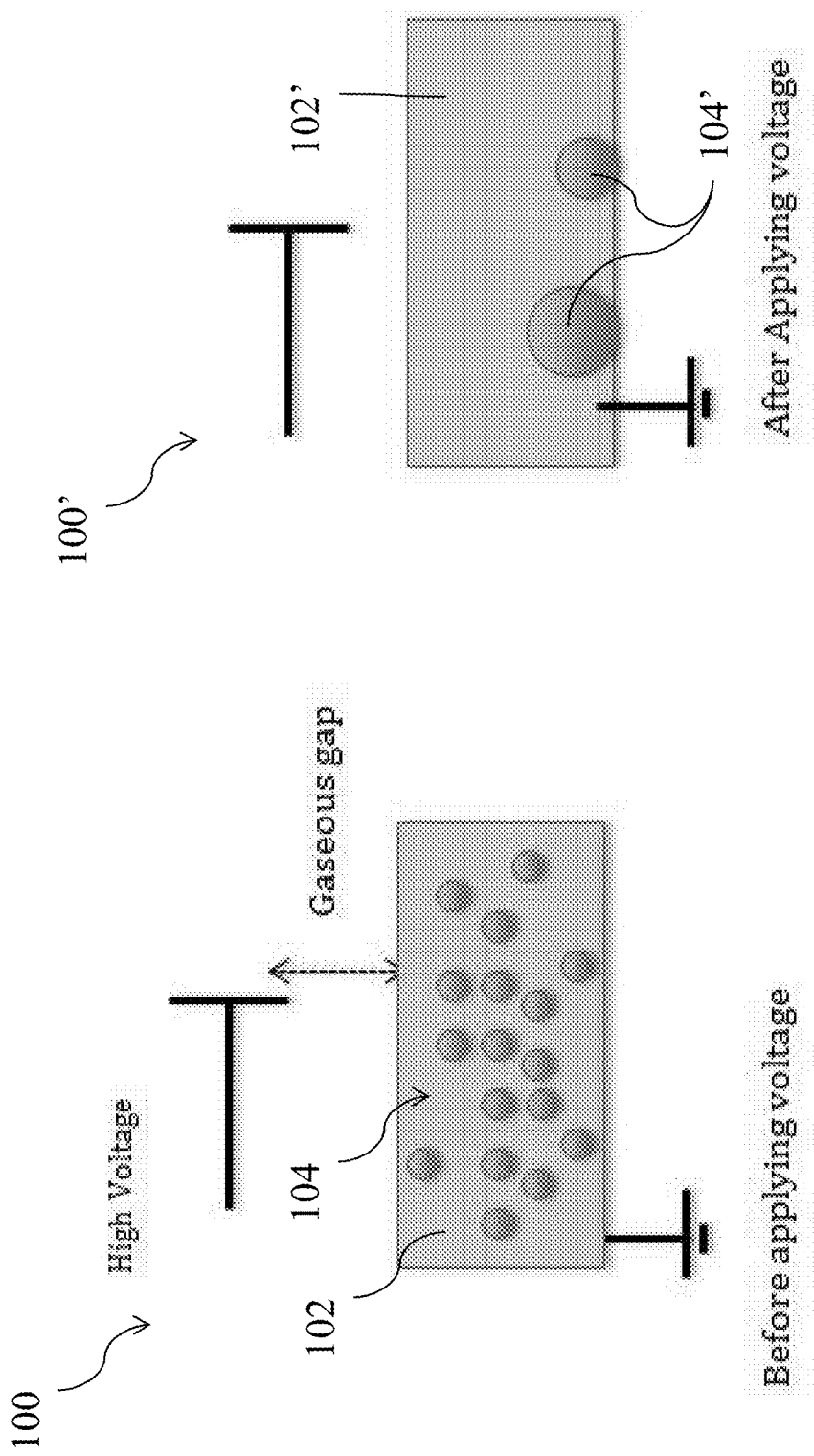
FIG. 1 is a schematic drawing demonstrating corona discharge of positive or negative ions targeting an emulsion interface to promote coalescence of droplets, in accordance with some embodiments of the invention.

It is contemplated that articles, apparatus, methods, and processes of the claimed invention encompass variations and adaptations developed using information from the embodiments described herein. Adaptation and/or modification of the articles, apparatus, methods, and processes described herein may be performed by those of ordinary skill in the relevant art.

Throughout the description, where articles and apparatus are described as having, including, or comprising specific components, or where processes and methods are described as having, including, or comprising specific steps, it is contemplated that, additionally, there are articles and apparatus of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously. Embodiments of the invention may be performed as part of a continuous, semi-continuous, or batch process.

It is contemplated that methods of the invention may be combined or supplemented with reactors, systems, or processes that are known in the art. Any known techniques for material separation, isolation, and purification may be adapted for application in processes encompassed by various embodiments of the invention, for example, techniques for distillation, extraction, reactive extraction, adsorption, absorption, stripping, crystallization, evaporation, sublimation, diffusional separation, adsorptive bubble separation, membrane separation, and/or fluid-particle separation. General information regarding separation processes and their design may be found, for example, in "Separation Processes," Klaus Timmerhaus, editor, in The Engineering Handbook, Section VIII, Richard C. Dorf, editor-in-chief, CRC Press, Inc., ISBN 0-8493-8344-7, pp. 579-657 (1995). It is also contemplated that methods, systems, and processes of the claimed invention may include pumps, heat exchangers, and gas-, liquid-, and/or solid-phase material handling equipment known to those of ordinary skill in the field of separations.

The mention herein of any publication, for example, in the Background section, is not an admission that the publication serves as prior art with respect to any of the claims presented herein. The Background section is presented for purposes of clarity and is not meant as a description of prior art with respect to any claim.

The embodiments described herein apply to separations of emulsions and other mixtures, including for example, (1) a mixture of two or more liquids that are immiscible, with one liquid phase being dispersed in the other liquid phase (e.g., oil-in-water emulsions; water-in-oil emulsions; oil-in-saltwater emulsions; saltwater-in-oil emulsions; particle-in-oil mixtures, etc.), where the dispersed phase has a particle size on the order of 1 nm-1000 nm or 1 µm-1000 µm; (2) gas and oil mixtures (e.g., bubble-in-oil mixtures); (3) foam-in-oil mixtures (e.g., where the foam is formed by coinjecting a surfactant with steam or with a non-condensible gas (e.g., nitrogen, nitrogen and steam); (4) emulsions comprising three phases (e.g., gas, liquid, and solid); (5) multiphase emulsions comprising three or more phases; (6) mixtures comprising any combination of liquids, solids, gases, bubbles, foam, and/or particles.

In some embodiments, the particle size is between 1-5 nm, 1-10 nm, 1-20 nm, 20-50 nm, 50-100 nm, 100-300 nm, 300-500 nm, 500-1000 nm. In some embodiments, the particle size is between 1-5 µm, 1-10 µm, 1-20 µm, 20-50 µm, 50-100 µm, 100-300 µm, 300-500 µm, 500-1000 µm.

In some embodiments, "saltwater" refers to water having a salinity of about 3.5%. In some embodiments, "saltwater" refers to water having a salinity between about 3.1% and about 3.8%. In some embodiments, "saltwater" refers to a brine (e.g., solution of salt (e.g., sodium chloride) in water) having a salinity between about 3.5% and about 26% at ambient conditions/

In some embodiments, the dispersed phase includes biological material. In some embodiments, the biological material includes biomolecules. In some embodiments, biomolecules include, but are not limited to, DNA, RNA, cells, enzymes, vaccines, proteins, amino acids, nucleotides, sugars, lipids, etc., whether naturally occurring or artificially created.

In some embodiments, the conductivity of the oil ranges between about $10^{-14}$ S/m (highly insulating) to $10^{-5}$ S/m (highly conducting). In some embodiments, the conductivity of the water or salty mixture is between about $10^{-7}$ S/m to about 100 S/m.

The emulsion separation methods discussed above may be integrated with existing skimmers in mixture separation plants. In some embodiments, the emulsion separation methods discussed below can be adapted to any separation system as a pre-treatment or post treatment step. In some embodiments, the system for separating emulsions discussed below can be used independently as separate separator.

In some embodiments, the systems and methods for separating emulsions discussed below can be integrated with gravitation separators, centrifugal separators, and the like. In some embodiments, the emulsions may be separated (completely or partially) during transport (e.g., transport on a conveyor belt or similar conduit). In some embodiments, the conveyor belt or conduit includes a texture or coating that helps promote the separation of the phases in the emulsion.

In conventional methods of electrically induced separation, it is assumed that positive attracts negative (e.g., that a positively charged droplet would attract a negatively charged droplet) while like-charge (positive-positive or negative-negative) repels (e.g., that a positively charged droplet would repel another positively charged droplet). However, methods are presented herein that apply a unipolar separation technique in which droplets of like charge (but different charge density) coalesce. Experiments described herein demonstrate that a single polarity is sufficient to induce coalescence of proximate like-charged droplets. Therefore, a new class of separators is proposed herein where the droplets coalesce based on like-charge attraction. Both the emulsion and the droplets are charged.

Without wishing to be bound to any theory, it is postulated that the non-uniformity of net charge for adjacent droplets causes Coulombic force. Exploiting Coulombic force induces omni-direction coalescence of droplets and eliminates the need for specific orientation for droplets respect to the external field. Since there is only one electrode immersed in the emulsion, the probability for undesired electrostatic breakdown can be practically eliminated. Various different embodiments fall within the unipolar electrostatic separation concept. Examples of such embodiments are described herein. Headers are provided for organizational purposes and are not intended to be limiting.

Coalescence is an important process in many fluid systems including raindrop formation, emulsions destabilization, liquid-liquid interface control in Lab-on-a chip devices, particle ordering in colloidal systems and atomization and spraying. In some embodiments, the spraying can be done by an atomizer, spray, electro-spray system, or a fog generator system. In some embodiments, conventional fog generators can be modified to generate unipolar charged droplets. Unipolar charged droplets can then be introduced to the target which could be emulsion/mixture. Electric fields induce coalescence of liquid drops. The electro-coalescence of adjacent droplets occurs in important processes such as storm clouds, dehydration of oil and emulsion breakdown in petroleum industries, electro-spraying in mass spectrometry, and ink-jet printing. In these processes, it has been assumed that oppositely charged masses attract and coalesce while like-charges repel and do not merge. However, recently it was shown that like-charge conductive hard spheres almost always attract each other when they are close enough but repel after the contact.

Counter-intuitively, in some embodiments discussed herein, it is demonstrated that two positively charged water droplets may attract and then coalesce. The mutual polarization of one droplet induces an image charge of opposite polarity on the other droplet causing a short-range attractive force. For near droplets with large enough charge difference, this short-range attractive force induces local deformations in both meniscuses at the nearest poles. After the meniscuses contact, a liquid bridge is formed between two deformed poles. This transient bridge is a conduit to exchange charge between droplets of like charge to minimize the electrostatic energy of the system of droplets. Initially, the current carrying liquid bridge is stabilized against the destabilizing effects of the surface tension through the Maxwell stresses exerted in both normal and tangential directions on the liquid bridge interface. This electrostatically supported liquid bridge, which is reminiscent of a "water floating bridge", temporarily holds two like-charge droplets connected. The liquid bridge then reverts to a regular capillary bridge as the electric field between droplets decreases. The capillary bridge develops and tends to minimize the surface of connecting droplets. As a result, coalescence of like-charge droplets may happen. Coalescence of like-charge water droplets should particularly influence understanding of emulsion separation.

Short-range attractive force arises due to redistribution of surface charge density and mutual polarization of non-equally charged "perfect" conductive spheres, as will be discussed in further detail below. Close enough like-charge spheres repel each other if they are brought or have been brought into contact, since, equipotential conductive spheres always repel.

As described herein, a droplet with a net and unipolar charge refers to a droplet for which the algebraic summation of negative and positive charges is non-zero. In certain embodiments, the volume charge density in a mixture (e.g., an emulsion) can be as small as $1$ $nC/m^3$. However, in certain embodiments, it can reach as high as $10$ $\mu C/m^3$ ($10^{-5}$ $C/m^3$) which is around the limitation of oil breakdown. In certain embodiments, the volume charge density is no less than $10$ $nC/m^3$, no less than $100$ $nC/m^3$, no less than $500$ $nC/m^3$, no less than $1$ $\mu C/m^3$, no less than $5$ $\mu C/m^3$, or no less than $10$ $\mu C/m^3$.

Previous methods that employ polarization forces exhibit a zero net charge on droplets (number of positive and negative charges are equal), and the volume charge density inside the emulsion/mixture is zero. A negligible amount of volume charge might be introduced in these systems around the electrode, but the whole volume experiences the electro-neutrality (thermodynamically in equilibrium except the regions around the electrodes where the electro-chemical effects cannot be neglected). In contrast to previous methods, embodiments described herein place the volume in a thermodynamically non-equilibrium state with non-zero space charge density.

Corona Discharge Bombardment of the Emulsion

In some embodiments, corona discharge may be used to destabilize the emulsion. In one example, a live high voltage wire lost its solid/oil-insulating jacket. Oil in the jacket spilled over a conductive countertop while a corona discharge emitted from the bare electrode. The leaked oil on the countertop expanded, while there was no similar effect observed on the water meniscus in an adjacent beaker. Corona discharge applied a force to the oil, but had no observable effect on a water interface. This observation prompted creation of a new separator based on corona discharge using a well-defined corona discharge set-up.

For example, in certain embodiments, at least two electrodes are used to establish corona discharge—a sharp electrode (emitter) and a blunt grounded electrode (collector). The grounded collector electrode is in contact with an oil/water (or other) emulsion, while a gaseous medium is located between the emitter electrode and the emulsion. In some embodiments, the gaseous medium can be air or other gases, or a combination of different gases and the system works with the gas within a wide range of temperatures and at a wide variety of pressure (e.g., below, at, or above atmospheric pressure). The embodiments discussed herein may be performed under any temperature and pressure conditions. In some embodiments, temperature and/or pressure may be determined based on the need for the quality of the discharge. In some embodiments, the breakdown voltage of the gas in the corona discharge embodiments discussed herein can be adjusted by changing the gaseous temperature/pressure depending on the elevation of the plant site with respect to the sea level. When an electric potential difference between a sharp and blunt electrode is applied above a certain voltage, e.g., the so-called corona discharge threshold, the imposed electric field becomes strong enough around the sharp tip such that the surrounding neutral gaseous molecules in the electrode separation region become partially ionized. A cloud of ions is generated and accelerated toward the low potential region. The charge is transferred across the gap due to the drift of charge carriers generated by the electric field. Therefore, the corona discharge is accompanied by a weak electrical current.

Corona discharge establishes a net and unipolar charge in the emulsion. In some embodiments, targeting the emulsion with unipolar ionic bombardment through corona discharge leads to separation of phases. For example, in some embodiments, one electrode is immersed in the emulsion, and the other corona discharge electrode is immersed in the air or gaseous medium above the emulsion interface. The gaseous medium may be at any temperature and pressure.

In some embodiments, the emulsion can be a mixture of different liquids, particles and liquids, proteins and DNA, cells, or any matter within an insulating liquid or dielectric liquid with low electrical conductivity. In some embodiments, the corona electrode is an electrode or systems of electrodes with sharp tip or tips. The corona discharge emits from the sharp tip or tips. In some embodiments, the corona discharge electrode can be a needle, multi-needles with different arrangements, sharp blade or blades, thin wire or multi-wires, wires coated with microstructures, nano-tubes (CNT) or nano-structures or any other sharp geometries. In some embodiments, the corona discharge needle is helical, sawtooth, or any other sharp point needle. In some embodiments, the electrode is preferably constructed from materials that are capable of withstanding the ionization-induced corrosion, thereby minimizing maintenance costs. In some embodiments, the gaseous medium in which the corona electrode(s) is fixed can be any gaseous medium such as nitrogen, oxygen, air, argon, helium or any other gases or combination of gases, at any pressure or temperature. In some embodiments, the collector electrode, which is immersed in the emulsion, can be, for example, a metallic bare electrode, a silicon substrate with native oxide, a metallic electrode with dielectric thin film coating, or the like. In some embodiments, the geometry of the immersed electrode can be planar, a three-dimensional (contoured) surface, a wire or wires, or a mesh, for example. In some embodiments, the immersed electrode can have any geometry or shape.

In some embodiments, the potential difference between the corona emitter electrode and immersed electrode (which can be grounded or can be at different potential) can be applied by a high voltage power supply. In some embodiments, at and above a corona discharge threshold voltage, by slightly increasing the voltage, a small current can be measured between the electrodes across the gaseous gap and the emulsion. This is a non-limiting example of a signature of the corona discharge. Another non-limiting example of a qualitative signature is an acoustic noise generated by the discharge phenomenon, which is sometimes accompanied by a blue-violet glow around the sharp tips. In some embodiments, corona discharge may or may not accompany with this glow depending on humidity and other factors. Increasing the voltage, one may increase the current across the emulsion and increase the volume charge density acquired by emulsion, in accordance with some embodiments of the invention.

In some embodiments, as soon as corona discharge is established, the size of the droplets begins to grow. In some embodiments, the growth rate is such that after a short period, large droplets can be visually observed in the bulk emulsion. This is evidence of a high rate of electro-coalescence. Note that either positive or negative polarity can be applied to the corona electrode. Choosing positive polarity, however, may increase the electro-dynamic stability of the discharge, in accordance with some embodiments of the invention.

An important difference between previous techniques and the unipolar techniques described herein is that adjacent droplets in the emulsion acquire net and unipolar charges. Therefore, here, the separation is based on strong coulombic force between charged droplets. For example, applying positive corona discharge results in droplets with positive charge, while applying negative corona discharge results in droplets in the emulsion with negative charge. The sharp electrode(s) is/are separated from the emulsion interface, and there is no electrical contact between the emulsion interface and the sharp emitter electrode, in accordance with some embodiments of the invention. Therefore, only a single polarity electrode is required to be in physical contact with the emulsion, in accordance with some embodiments of the invention. Having only one polarity inside the emulsion is advantageous, in accordance with some embodiments of the invention. In some embodiments, this may significantly reduce the chance of electrostatic events, particularly because the main voltage drop occurs across the gaseous gap, not within the emulsion. Moreover, the amount of charge injected into the emulsion is independent of oil breakdown strengths because the electrode has no ohmic contact with the emulsion, and a large volume of charge may be locally injected into the emulsion. This leads to further non-uniformity in the field and an increase in the incidence rate of droplet coalescence.

Furthermore, in some embodiments, the method can be effective even with highly conductive emulsions (e.g., where salt concentrations in the aqueous phase are high), since the charge is generated outside of the emulsion. Thus, in some embodiments, the amount of current is primarily dictated by discharge properties in the gaseous gap and is less dependent on the emulsion. Therefore, the embodiments discussed herein can be adapted to any oil-water mixture with any quality of oil or water. It should be noted that the content of salt in water is also not important for achieving successful results and desired coalescence levels.

In some embodiments, coalescence of droplets of salt water solution of high salt content (e.g., >0.5 M, >1.0 M, >1.5 M, or >2 M) can be observed in an emulsion with silicon oil. Conventional electro-coalescencers are designed specifically for quality of oil/water based on oil/water and the salt contents—and these can vary region to region. However, using some embodiments described herein, one can control both applied voltage and current by changing the pressure of the gaseous medium, increasing the voltage at the source, and/or varying the time of corona exposure to adapt the technique for a desired separation output with oil/water emulsions having different qualities (e.g., different salt contents). The process is easily adapted and controlled for application to a wide variety of emulsion compositions and separation needs.

Without wishing to be bound by a particular theory, the mechanism of unipolar separation appears to follow a newly-discovered phenomenon of attraction between like-charges in an insulating medium. It has been speculated that like-charge particles may attract; however, it has remained an outstanding question.

Two charged conducting hard spheres almost always attract each other if they are close enough. See Lekner, John, "Electrostatics of two charged conducting spheres," Proceedings of the Royal Society A: Mathematical, Physical and Engineering Science 468.2145 (2012): 2829-2848, incorporated herein by reference in its entirety. Attractive force arises due to the mutual polarization of spheres and redistribution of the surface charge density over one of these spheres. As two positively charged spheres approach closer, one gets a negative charge density at the pole closest to the other sphere, and then the other acquires an increased positive charge density at its neighboring pole. This attractive force increases without limit as two spheres are approaching together. The localized attraction of near charges wins over the overall repulsion of coulombic force between the two like-charge spheres, and they attract each other. One theoretical exception to the principle discussed above is when the two spheres have the same charge ratio that they would obtain by being brought into contact. In this case, two spheres repel. Presented herein are applications of this principal in the coalescence of like-charged droplets having different charge ratio for separation of phases of an emulsion, as evidenced by experimental results presented herein.

Experimental Set-Up and Examples

Direct Ion Injection—Corona Discharge

FIG. 1 is a schematic drawing demonstrating corona discharge of positive or negative ions targeting an emulsion interface to promote coalescence of droplets, in accordance with some embodiments of the invention. The schematic 100 on the left shows a schematic drawing of the emulsion 102 with a number of droplets 104 dispersed throughout the emulsion 102 prior to applying a voltage. The schematic 100' on the right shows a schematic drawing of the emulsion 102' after applying the voltage—as seen in this schematic, at least some of the droplets 104 coalesced forming larger droplets 104'. The ionic bombardment due to the corona discharge may directly inject the created ions into the emulsion volume from the interface. The electrification of the emulsion occurs from an external source (corona discharge). The ions are generated outside of the emulsion and are directly injected into the volume from the emulsion/air interface. The ions distribute in the emulsion and droplets acquire net charge but with the same polarity. Corona discharge creates highly non-uniform single polarity charges in the emulsion. Without wishing to be bound to any given theory, it is believed that the difference of charge between adjacent droplets causes attraction and eventual merging of droplets. By increasing the time of exposure, the oil can be separated from water by coalescing the small water droplets and growing the droplet sizes.

Figure 2:
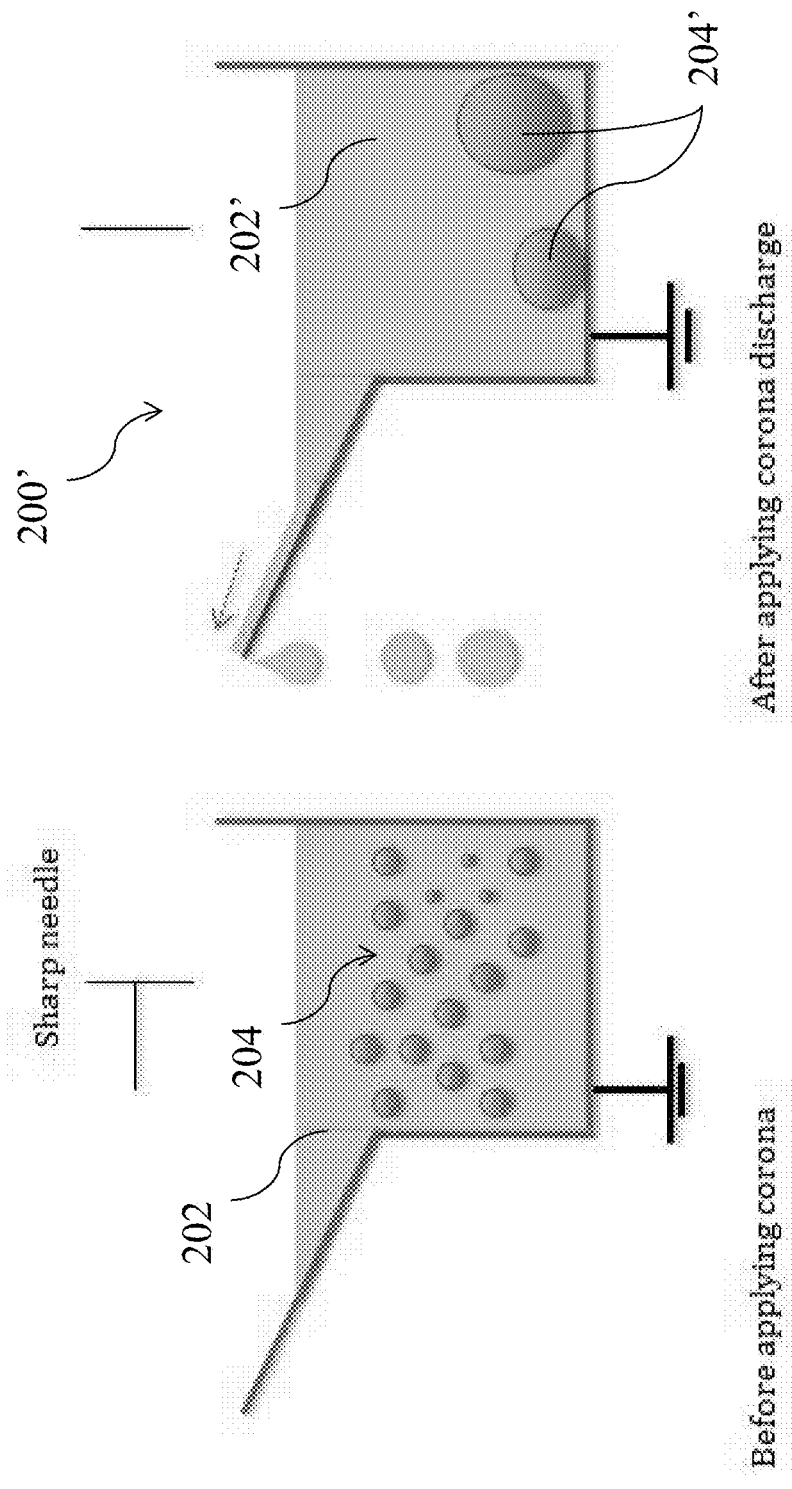
FIG. 2 is a schematic drawing showing a corona discharge system for separation of two or more phases of an emulsion to simultaneously promote droplet coalescence and pumping/spreading effect for phase separation, in accordance with some embodiments of the invention.

FIG. 2 is a schematic drawing showing a corona discharge system for separation of two or more phases of an emulsion to simultaneously promote droplet coalescence and pumping effect or differential spreading phenomenon for phase separation, in accordance with some embodiments of the invention. The schematic 200 on the left is a schematic drawing of an emulsion 202 with a number of droplets 204 dispersed throughout the emulsion 202 prior to application of corona discharge. The schematic 200' on the right is a schematic drawing of an emulsion 202' after applying corona discharge to the emulsion, which caused at least some of the droplets 204 to coalesce and form larger droplets 204'.

In some embodiments, the corona discharge electrode system may be designed so that it takes advantage of both (i) the separation of water droplets (or other phases) out of the emulsion due to like-charge electro-coalescence, and (ii) the physical pumping/spreading/moving of the oil-rich phase away from the water-rich phase (or other remaining phase), e.g., out of the emulsion container. Because the 'pumping' or spreading effect occurs with oil and not with water, the differential effect can be exploited for further separation efficiency, in accordance with some embodiments of the invention.

In one embodiment, a tank of emulsion is equipped with a protruding edge (ramp) which serves as a low voltage electrode. A sharp electrode is positioned above the tank and is used to establish the corona discharge. Emulsion may be added to the tank in a continuous, semi-continuous, or batch-wise manner. The corona discharge from a single or multiple electrode may physically move or pump the purified oil phase up the ramp and direct it to another container or conduit for retaining the purified oil separated from the emulsion. The separated aqueous phase may remain in the bottom of the tank where it can be drained.

In some embodiments, one or more of the corona discharge emitter electrodes are placed around the ramp to exploit the corona discharge pumping effect. While electro-coalescence is occurring inside the bulk, the purified oil is pumped up by an appropriate configuration of electrodes. A higher salt content in the aqueous phase of the emulsion may even be favorable here, since it may enhance the contrasting electrical conductivities between the oil phase and the aqueous phase, in accordance with some embodiments of the invention.

Unipolar Charge Transfer by Mass Transfer—Spraying Unipolar Charged Droplets into the Emulsion In corona discharge embodiments, the charge is introduced directly by ionization of gaseous molecules. However, one may deliver unipolar charges into the bulk emulsion via a charged mass. For example, spraying unipolar charged drops, or a stream, into an emulsion may result in the emulsion acquiring a net and unipolar charge such that adjacent droplets therein acquire net and unipolar charges. In some embodiments, spraying takes place via electro-spraying or mechanical spraying (e.g., atomization).

Figure 3:
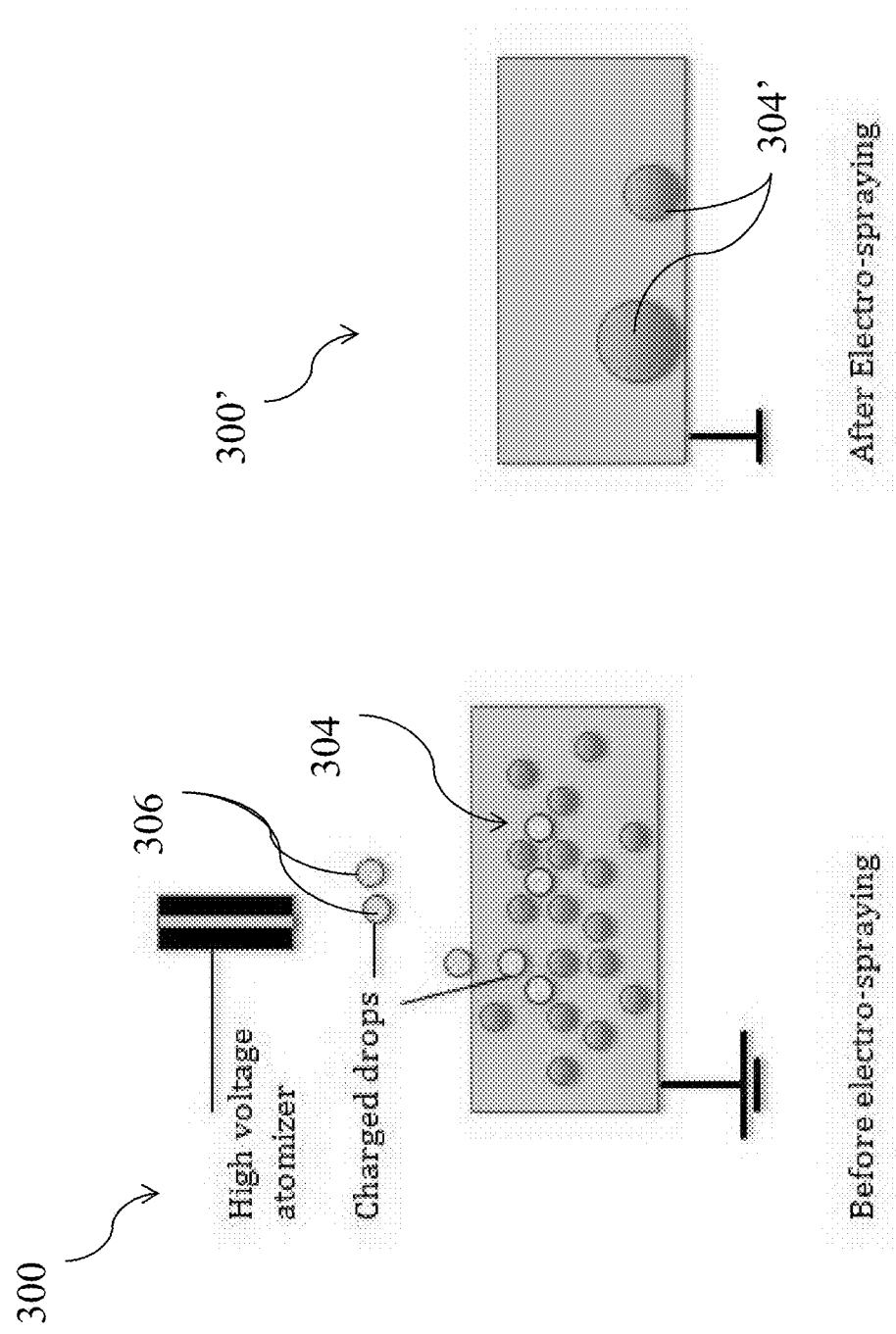
FIG. 3 is a schematic illustrating a system for spraying unipolar charged droplets 306 into an emulsion 302 for separation of the emulsion phases, in accordance with some embodiments of the invention.

FIG. 3 is a schematic illustrating a system for spraying unipolar charged droplets 306 into an emulsion 302 for separation of the emulsion phases, in accordance with some embodiments of the invention. The schematic 300 on the left shows the emulsion 302 with a number of droplets 304 dispersed throughout the emulsion 302 prior to electro-spraying. The schematic 300' on the right shows the emulsion 302' after electro-spraying, which caused at least some of the droplets 304 to coalesce forming larger droplets 304'.

FIG. 3 is a schematic showing a system for spraying unipolar charged drops into an emulsion for separation of the emulsion phases. In some embodiments, electrostatic atomization of insulating oil or water may be used and the cloud of small, charged droplets may be directed into the emulsion. In some embodiments, the injected atomized liquid may be chosen based on composition of the emulsion to be separated. For example, for a water-in-oil emulsion, where water is the dominant phase, in some embodiments, oil can be atomized. In some embodiments, the liquid droplet with unipolar net charge in the emulsion may transfer the charge through a conduction and/or convection mechanism to the emulsion. The native water droplets in oil acquire these charges, and the mechanism as discussed with corona discharge can occur and cause the electro-coalescence of unipolar charged droplets. Different configurations of electrodes can be used; for example, circular nozzles, rectangular atomizers, single- or multiple-atomizers can be used.

Pouring Bath of Unipolar Charged Liquid into Emulsion

In another non-limiting embodiment of unipolar charge transfer via mass transfer, an amount of the emulsion is charged first then introduced into a larger quantity of the emulsion. For example, corona discharge can be used in some embodiments to inject charge into a bath including a portion of the emulsion. Then, the bath of charged liquid or mixture is introduced into a larger batch or stream of the emulsion where separation is performed. The charged liquid diffuses into the emulsion and transfers charge by both conduction and convection. Unipolar charge transferred by mass transport and electric conduction may cause coalescence of droplets in the bulk so that the droplet size of the dispersed phase grows. The separated droplets are large enough to sediment and collect in the bottom of the batch. This method can be combined with gravitational separation to expedite the separation process. Pure oil can be charged and pour into the gravitational separator tanks. The unipolar electro-coalescence occurs due to the unipolar separation.

Tribo-Electrification: Unipolar Separation Technique

In some embodiments, tribo-electrification is used to perform unipolar emulsion separation. This method is an alternative to corona discharge exposure and spraying of unipolar charged droplets into an emulsion. It is as simple as the corona discharge technique, but it may eliminate the need for an active power supply, in accordance with some embodiments of the invention.

For example, in some embodiments, a charge is transferred into an emulsion by passing it through a polymer pipe made from PMMA or other tribo-electric material. In some embodiments, the pipe interior surface may be coated with a polymer or a combination of polymers such as PMMA, PVC, or the like. Passing the emulsion over the surface may create a unipolar volume charge inside the emulsion due to the friction between the pipe and the emulsion. This unipolar charge may result in an increased droplet size due to unipolar electro-coalescence. For example, in some embodiments, this concept can be applied to gravitational towers where increasing the size of water droplets may cause significantly faster separation. In some embodiments, it may be sufficient to simply pass the emulsion over a proper tribo-electric material so that the droplets become charged. In some embodiments, the gravitational tower, separation column, or other container should be electrically insulated so that the charge remains in the separator.

Observations

Methods described herein may be combined with current oil/water separation processes without substantial changes in their layouts. Existing systems may be retrofitted with a unipolar charge separation stage or module, for example, as described herein.

Demonstrated herein are new separation techniques in which unipolar droplets attract each other. Unlike previous dielectrophoretic techniques, here the active mechanism is electrophoretic force. Experiments verify the like-charge attraction of dispersed droplets in a background phase. This attraction causes coalescence of droplets, thereby affecting separation of phases of the emulsion. The concept can be applied to separate droplets in emulsions, as well as solid particles in suspensions. The applications include, but are not limited to, separation of water/oil emulsions, as well as separation of cells, proteins, DNA, and other kinds of mixtures.

In certain embodiments, only the collector electrode(s) is/are immersed into the emulsion/mixture, and the emitter electrode is outside the emulsion/mixture. In certain embodiments, the mixture acquires a net charge. Therefore, unlike the conventional method where volume charge is negligible, in our method, volume charge is essential, and in certain embodiments it is as at least 1 $nC/m^3$, at least 10 $nC/m^3$, at least 100 $nC/m^3$, or at least 1 $\mu C/m^3$.

An advantage of methods presented herein is that the high voltage electrode has no contact with the emulsion. Since the main voltage drop occurs across the gap, the chance of arc or electrostatic breakdown can be significantly reduced. Moreover, in the embodiments involving spraying unipolar charged droplets into the emulsion or tribo-electrification of the emulsion, the probability of electrostatic breakdown is significantly reduced while maintaining unipolar charge in the bulk.

Another advantage of the proposed method using corona discharge is that large volume charge densities can be injected into the emulsion so that there is strong non-uniformity of the electric field in the non-homogenous emulsion medium. This non-homogeneity in the field may cause potential difference between like-charge droplets and this may increase the chance of coalescence. Moreover, in some embodiments, physical separation of water/oil emulsion phases is enhanced by corona discharge because the purified oil is pumped (or pumping is assisted) by the electrostatic pressure while the electrostatic pressure on the conductive aqueous phase is zero. This can be a particularly important embodiment for separation of a mixture in a micro-gravity condition, for example, where power is limited and a gravitational field is absent. Gravitational separation cannot be used in micro-gravity, while corona discharge embodiments can be a replacement of such methods. Enhanced coalescence rate along with a pumping oil phase may result in generation of larger water droplets with lower oil contaminations with minimal power consumption, even in outer space applications.

Electro-coalescence does not appear to depend on orientation of droplets with respect to the electric field in the embodiments described herein. In conventional methods, droplets must be oriented in the field so that attractive force is generated. In those electro-coalescers, small deviation of the droplet may cause repulsion between droplets and stabilization rather than the desired separation. In contrast, in the embodiments described herein, electro-coalescence is omni-directional. Direction and orientation is not a requirement since the electrophoretic force can be exerted in any direction.

Experiments show the effectiveness of the corona discharge systems described herein for both water-in-oil emulsions and oil-in-water emulsions. In certain embodiments, phases of emulsions with average droplet size <50 microns, <25 microns, <10 microns, <1 micron, <0.5 micron or <0.1 micron can be separated. In certain embodiments, the range of applied voltage can be from about 1 to about 20 kilovolts (e.g., a few kilovolts) while the gap spacing between the electrode and interface of emulsion can be from about 0.1 mm to about 50 mm (e.g., on the order of tens of millimeters). In some embodiments, the applied voltage and the gap can be varied in larger ranges than presented above, but the resulting field should be large enough ($\sim 10^5$-$10^7$ V/m) to cause corona discharge from the tip of corona electrode. "Peek's law" may provide a first approximation of applied potential for a given gap spacing and a given gaseous pressure and temperature, but the potential also depends on the radii of curvature of the corona tip. The corona current and number of corona tips may vary depending on geometry and number of tips, but for a single tip the corona current is in the range of about 0.1 to about 200 microamp. Increasing the time of exposure may cause enhanced purification, but as little as 1 to 30 seconds is sufficient to produce satisfactory coalescence in certain embodiments. The corona discharge separation can also be conducted in multiple stages. At each stage, one may use different corona voltages with different configurations. However, one stage of exposure might be enough.

In certain embodiments, the container for the emulsion, itself, (or a portion thereof) serves as grounded electrode, and can have different shapes. It can be a flat electrode, an inclined flat electrode, a contoured electrode, or a curved electrode, for example. The emulsion can be stagnant or it may flow in an open channel.

The electrophoretic forces can collect the purified oil directly or it can be a dead-end system. The corona discharge exposure can be performed as a pre-treatment step for use in an existing system (e.g., a retrofit of a gravitational and/or sedimentation emulsion separation process), or it can be easily combined with other techniques. For example, the corona discharge exposure may promote coalescence between small droplets to form larger droplets, which are then more easily handled by current separation systems (e.g., gravitational, sedimentation, and/or chemical additive separation processes).

In some embodiments, the methods disclosed above can be combined with each other if required. In some embodiments, these methods can be combined with other traditional techniques, electrostatic existing techniques, gravitational, filtration or other techniques as pre-steps or post-process steps depending on required quality of the output purified phase and background.

In some embodiments, in order to increase the safety to a required degree, one may replace the gaseous phase with any other gases, for example, inert gasses. The technique is not limited to any particular pressure or temperature of the gas or emulsion, allowing for a more versatile separation process.

In some embodiments, the method may be applied to cause coagulation of solid particles, such as mud, sand, or the like in petroleum or in a biological medium. Similarly, coagulation can be achieved for cells, proteins, DNA, or RNA coagulation (or coagulation of other genetic material) by unipolar charging of a mixture containing such components.

Coalescence of Like-Charged Droplets

Figure 4A:
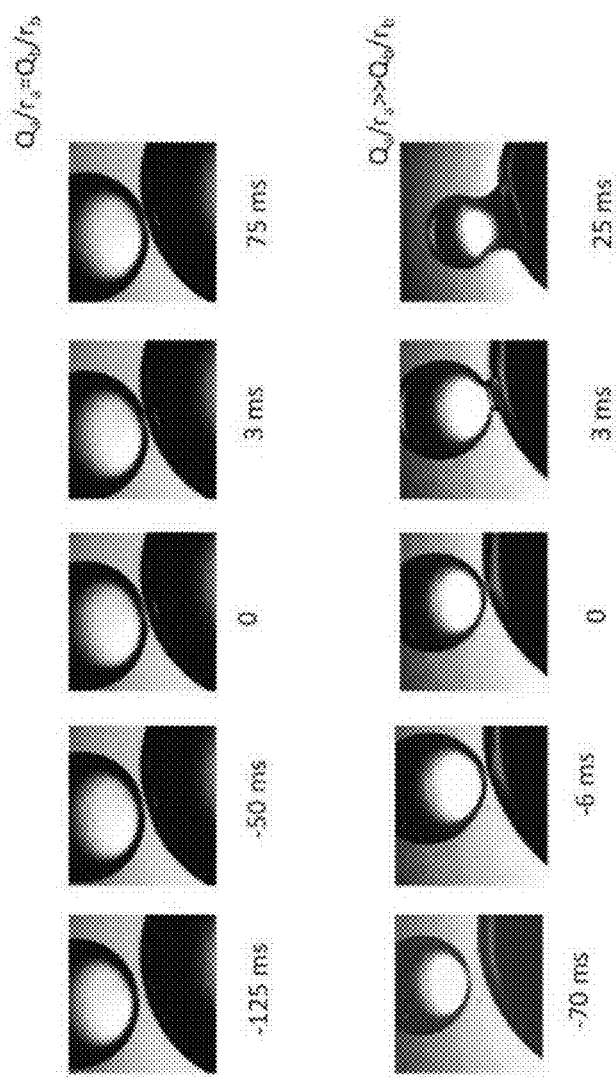
FIG. 4A shows a series of micrographs of two droplets of deionized water in silicon oil obtained at various times in relation to contact (t=0) of two like-charged (positively-charged) droplets, in accordance with some embodiments of the invention.

FIG. 4A shows a series of micrographs of two droplets of deionized water in silicon oil obtained at various times in relation to contact (t=0) of the two like-charged (positively charged) droplets. Qa is the charge of droplet a, Qb is the charge of droplet b, $r_a$ is the radius of droplet a and $r_b$ is the radius of droplet b. Attraction of droplets and coalescence is observed where the charge densities of the droplets are different, e.g., for example where Qa/ra>>Qb/rb, and where the droplets are sufficiently close to each other.

Figures 4B, 4C:
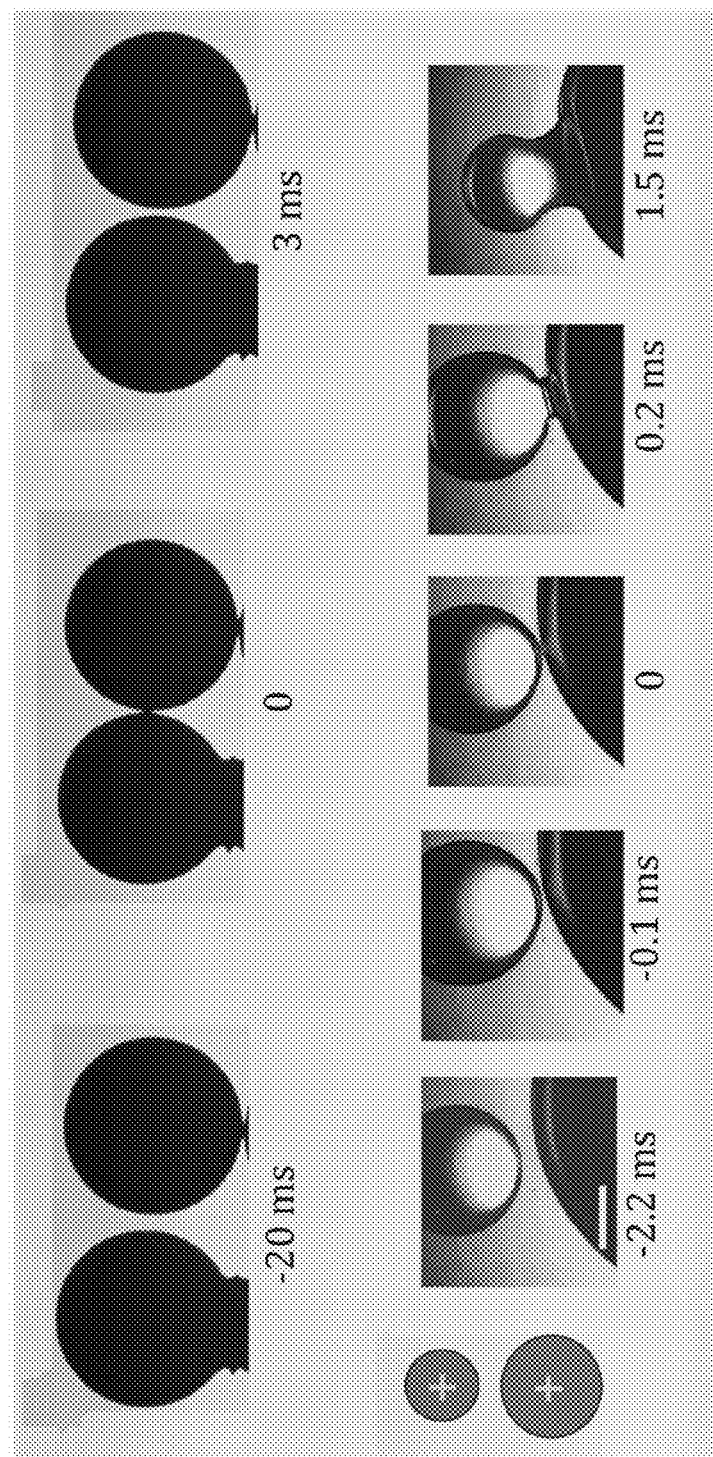
FIG. 4B illustrates electrostatic interactions of positively charged metal spheres in oil, in accordance with some embodiments of the invention.
FIG. 4C illustrates electrostatic interactions of like-charge water droplets in oil, in accordance with some embodiments of the invention.

FIG. 4B presents the experimental results for electrostatic interaction between two positively charged isolated metal spheres of the same size at close separations. It was observed that the positively charged spheres attract each other when the difference in magnitude of the charge between the spheres is large enough. As the charge difference is established, the attractive force pulls the right sphere towards the fixed sphere on the left. After a brief contact, the two spheres become equipotential and then repel each other. This observation confirms a recent prediction for attraction of conductive hard spheres carrying like-charges and the repulsion after the contact.

FIG. 4C shows a series of micrographs of electrostatic interaction of like-charge water droplets of different size carrying positive charges in a bath of oil with sufficiently large charge differences. The charges at the top and bottom droplets were +10.7 pC and 0.94 pC, respectively. Similar to metal spheres discussed in relation to FIG. 4B, two non-equipotential droplets with a large enough charge difference attract at close separations. However, after the contact at t=0, unlike the metal spheres of FIG. 4B, two droplets attract each other and coalesce as shown in FIG. 4C. Like-charge droplets slowly approach, and coalescence occurs immediately after the apparent contact at the nearest poles. The scale bar shown in FIG. 4C is 0.5 mm. The background oil is 450 centistokes silicone oil.

Figure 5:
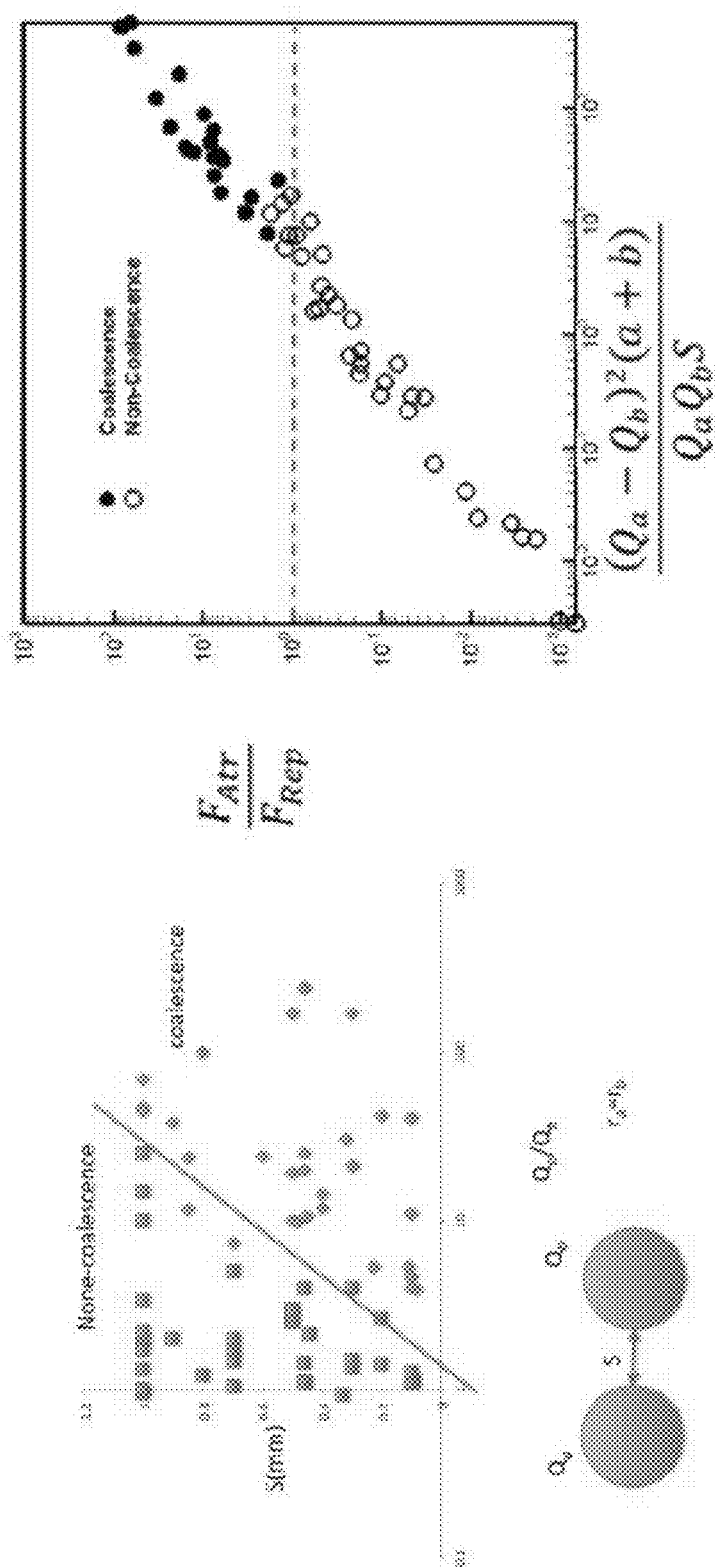
FIG. 5 shows experimental data demonstrating conditions for coalescence of like-charged droplets, in accordance with some embodiments of the invention. Filled circles denote coalescence and open (unfilled) circles represent non-coalescence of droplets.

FIG. 5 presents experimental data showing that coalescence of two like-charged droplets occurs when Coulombic force (FAtr/FRep) is roughly >1. Where the magnitude of the difference in like charges between the two droplets is greater (e.g., where Qa/Qb is higher), coalescence is observed between droplets at greater distances from each other, up to about 1 mm apart.

FIG. 6A depicts the result of charge measurements for two positively charged near droplets of the same size at a fixed initial separation of 50 μm. The initial separation is the gap between the neutral droplets before charging. As it is shown in FIG. 6A, a small charge difference between droplets is enough to cause electro-coalescence of droplets according to some embodiments of the invention.

In contrast, FIG. 6B illustrates that for two electrically connected identical water droplets, it is observed in some embodiments that droplets do not merge even if they are mechanically pushed together. This is attributed to the fact that the droplets become equipotential upon contact and the charge difference then equals zero. For identical spheres, a=b, the expression for the short-range attractive force between like-charge conductive spheres with net positive charges of $Q_a$ and $Q_b$ was obtained as $$F_{Atr} = -\frac{\{Q_a - Q_b\}^2}{8\pi\varepsilon_0 \alpha S \left\{\ln\left(\frac{4\alpha}{S}\right) + 2\gamma\right\}^2} \quad (2)$$

$\varepsilon_0$, S and γ are medium permittivity, the separation between droplets and Euler's constant, respectively. From Eq. (2) above, it can be inferred that close enough spheres of the same size always attract if and only if $Q_a \neq Q_b$. Whereas, for two identical spheres with precisely the same charges, a=b and $Q_a = Q_b$, the attractive force is zero. In this case, equally charged spheres become equipotential and repel. For equipotential spheres at close separations, the repulsive force, $F_{rep}$, is independent of the separation and can be obtained by Kelvin's formula:

$$F_{rep} = -\frac{1}{4\pi\varepsilon_0} \frac{Q_a^2}{(2\alpha)^2} \frac{4\ln 2 - 1}{6(\ln 2)^2} \quad (3)$$

Although the experimental results shown in FIGS. 6A, 6B, and 6C can be interpreted by the expression for attraction of like-charge presented in Eq. (2) above, it is still not clear why the unequally charged droplets coalesce after contact. In order to investigate the mechanism of coalescence, a high-resolution high speed imaging of droplet coalescence was performed immediately before and after contact.

FIGS. 7A-7C show a mechanism that occurs upon coalescence of two like-charged droplets in an emulsion. At t=20 microseconds, an electrostatic bridge appears, and, without wishing to be bound to any particular theory, appears to thicken into a capillary bridge, resulting in coalescence of the droplets.

FIGS. 8A, 8B, and 8C illustrate the behavior of like-charge DI water droplets in silicone oil in a series of sequential high-speed images at 180,000 frames s$^{-1}$. For two neighboring like-charge droplets, the droplet with larger absolute positive charge (top droplet) polarizes the other droplet with smaller net positive charge (bottom droplet). FIG. 8D represents a cartoon of electrostatic interactions for attraction and coalescence of like-charge droplets. The cartoon is based on experimental visualizations presented in FIGS. 8A-8C.

As shown in FIG. 8D, the batch of negative image charge (gray cloud) appears at the nearest pole of the droplet with smaller positive charge (pink cloud). The electric field between poles of nearby droplets increases as a result of local charge redistribution. The attraction between the positively charged meniscus and its negative image charge on the nearest pole of the other droplet meniscus causes attraction between droplets.

As can be seen in FIGS. 8A, 8B and 8C the attractive force induces Taylor cone-like deformation due to local enhancement of Maxwell stresses in the nearest poles where the electric field is strong. Both droplets and the two deformed meniscuses approach together. As the two meniscuses approach, the electric field becomes even stronger, and the enhanced field redistributes the charge and its image causing more pronounced deformations in the meniscuses. The deformed meniscuses finally touch each other, and a liquid bridge is immediately formed between the two droplets.

For droplets with small separations as presented in FIG. 8A, the formation of the bridge immediately after contact leads to high local curvature of the neck between connecting like-charge drops. The formation of the curved neck creates a local low-pressure region resulting in an inward flow towards the bridge. The inward flow supplies liquid to the bridge and fattens the neck; thus, the coalescence of like-charge droplets proceeds. For such small separations, the bridge morphology at its early evolution, t=0, cannot be captured with a proper optical resolution due to its small sizes. In order to visualize the details of evolution with reasonable resolutions after the contact, the initial separation between the droplets was increased as can be seen in FIGS. 8B and 8C In order to establish the like charge attraction and coalescence for the new larger separations, the absolute magnitude of the charge and the charge difference between drops were increased. The charge on the top droplet was increased near its Rayleigh limit while the charge on the bottom droplet was kept small. For these larger initial separations, the electro-coalescence also happens. It was observed that the two droplets attract each other and their meniscuses are deformed at their nearest poles. As the two deformed meniscuses contact, a remarkably stable transient liquid bridge is formed. The high aspect ratio liquid bridges clearly differ from the conventional capillary bridges. Such transient liquid bridges are reminiscent of the previously reported floating water bridges in air and the electrically supported high aspect ratio columns of slightly conductive liquids. Similar to the water floating bridge, since the permittivity of the liquid bridge is larger than the permittivity of the medium (oil in our case), $\in_w > \in_o$, the current carrying liquid bridge is stabilized by the normal and tangential electrostatic Maxwell stresses in the bridge. Both electrostatic and polarization force tends to "level" the bridge against the destabilizing effects due to the surface. Such stable liquid bridge holds two droplets electrically connected. Initially, when the electric field across the bridge is large, the liquid bridge between two charged droplets is stabilized by the electric field. As the charge transfers across the bridge, the tangential field between oil/water interfaces along the bridge gradually decreases. Subsequently, the electrostatically supported bridge reverts to capillary bridge. A capillary bridge between connecting droplets tends to minimize the surface of the connecting bodies. The formation of a self-sustained current carrying bridge and its transformation to capillary bridge favor the coalescence of two connecting droplets. For highly charged neighboring droplets, before the meniscus contact, electro-spraying occurs due to the intense tangential stresses exerted to the deformed pole. Even in the presence of such cone-jetting and electro-spraying between highly charged droplets, the like-charge coalescence proceeds. This implies that coalescence of like-charges is a general phenomenon and it may happen for wide ranges of charge magnitudes.

Figure 9:
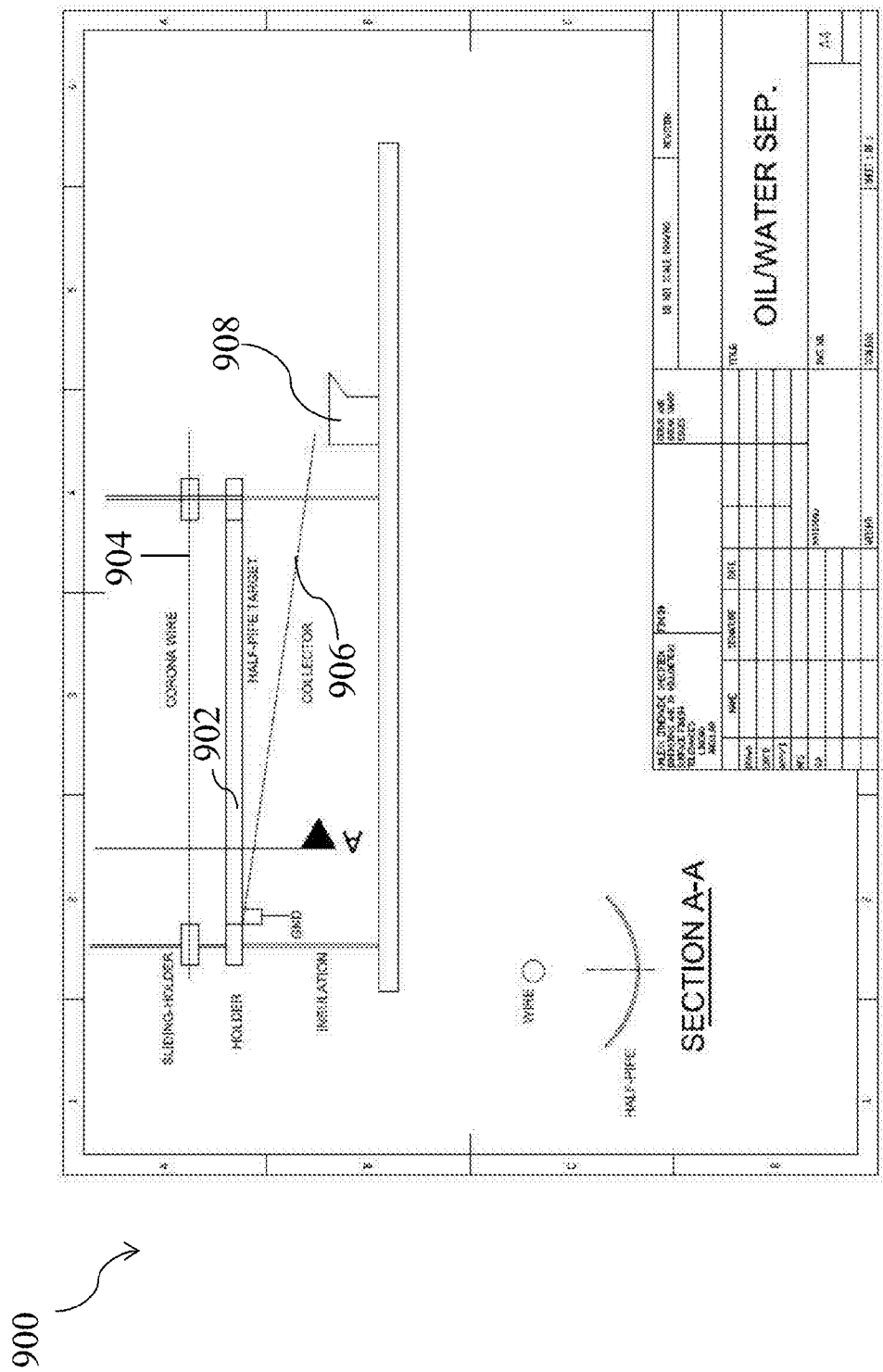
FIG. 9 is a schematic for an emulsion separation system 900 using corona discharge, in accordance with some embodiments of the invention.
Figure 10:
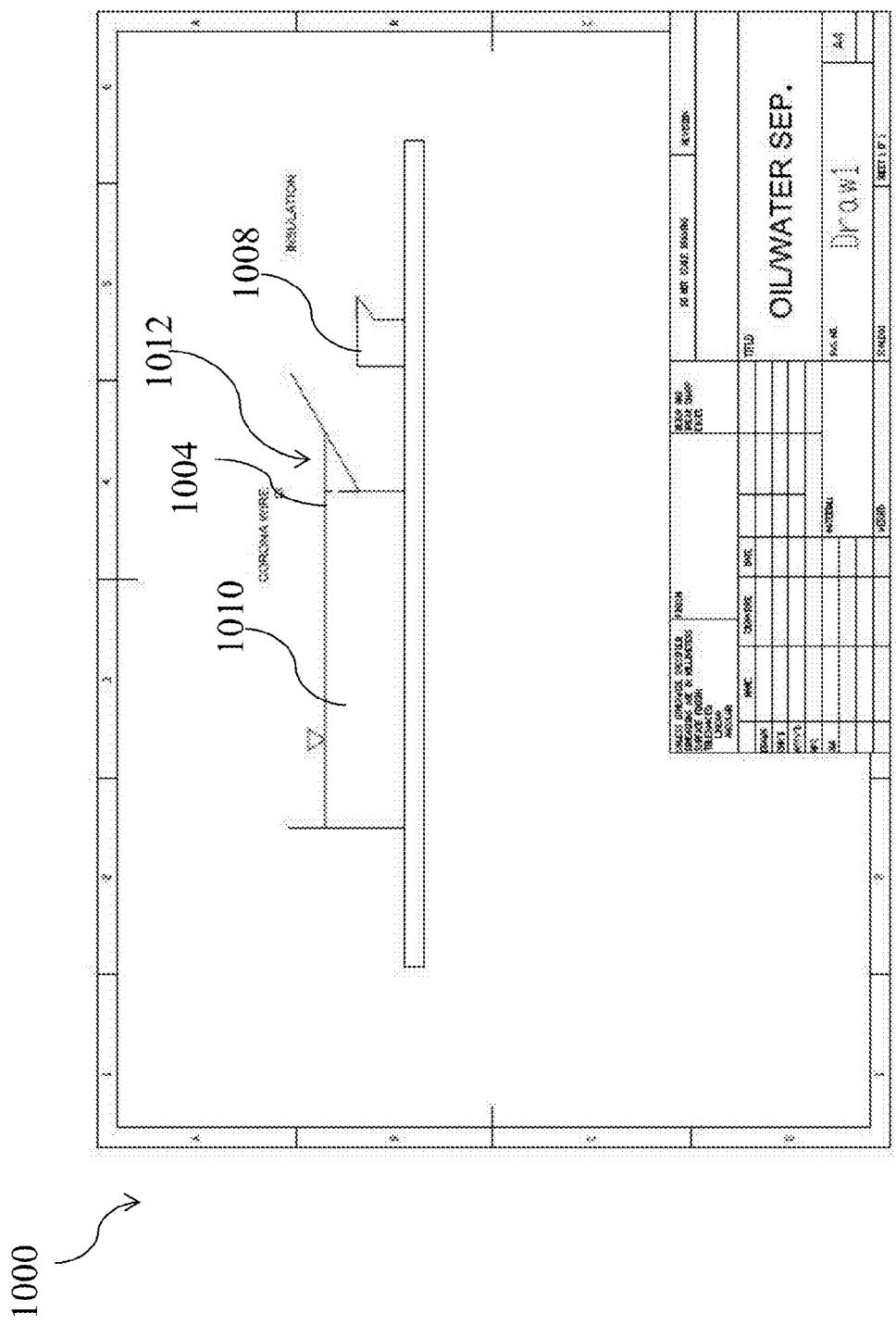
FIG. 10 is a schematic for an emulsion separation 1000 system using corona discharge, in accordance with some embodiments of the invention.

FIGS. 9 and 10 show two example schematics of oil/water emulsion separation systems that employ like-charged droplet coalescence as described herein.

In FIG. 9, an emulsion flows in a half pipe 902 below a corona wire (emitter electrode) 904. In some embodiments, the half pipe 902 may contain or may itself be a grounded collector electrode. The separation occurs during flowing of the emulsion along the half pipe 902. Differential spreading/pumping of the oil phase as a result of corona discharge forces the oil phase over the edge of the half pipe 902, and down a collector ramp 906 into a collection vessel 908. Instead of a half pipe 902, another channel of different geometry could be used, for example. In certain embodiments, multi-branch half pipes can be used, equipped with corona wires above the emulsion/air interface.

In the embodiment shown in FIG. 10, an emulsion fills a tank 1010. A corona wire 1004, corona blade, or any other type of sharp emitter electrode is placed above the tank near a ramped or tilted side or lip 1012 of the tank 1010. Differential spreading/pumping of the purified oil phase results from the corona discharge and forces the oil phase (and not the water phase) over the lip and into a collection vessel 1008. In some embodiments, the tank may be filled constantly with emulsion while corona discharge separates the phases and the pure oil is collected. Alternatively, in some embodiments, the tank may operate in batch mode or semi-batch mode. For large scale systems, in some embodiments, multiple high voltage electrodes can be used.

In some embodiments, tribo-electrification is used instead of corona discharge to produce the unipolar conditions leading to separation of the phases of the emulsion.

Figure 11A:
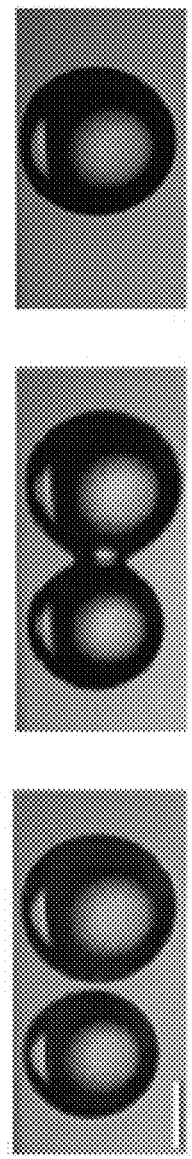
FIG. 11A illustrates a unipolar electro-coalescence of a system of two DI water droplets, in accordance with some embodiments of the invention. The applied voltage and current were +7 kV and 1 µA, respectively.
Figure 11B:
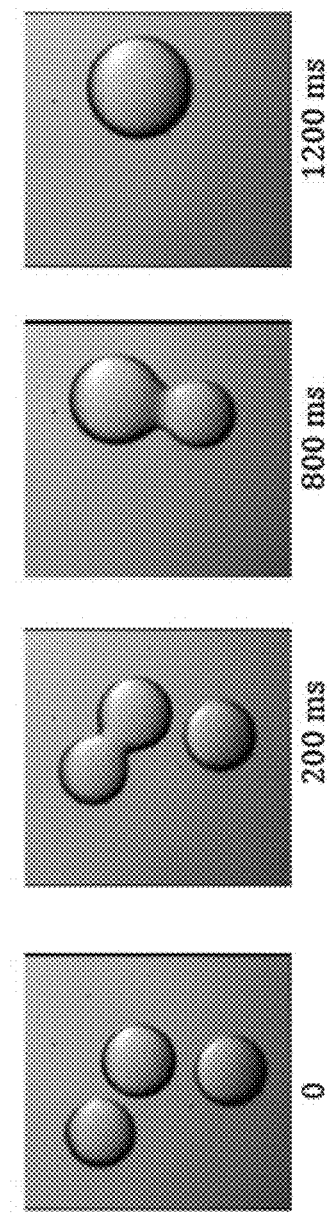
FIG. 11B illustrates a unipolar electro-coalescence of a system of three DI water droplets, in accordance with some embodiments of the invention. The applied voltage and current were +7 kV and 1 µA, respectively.
Figure 11C:
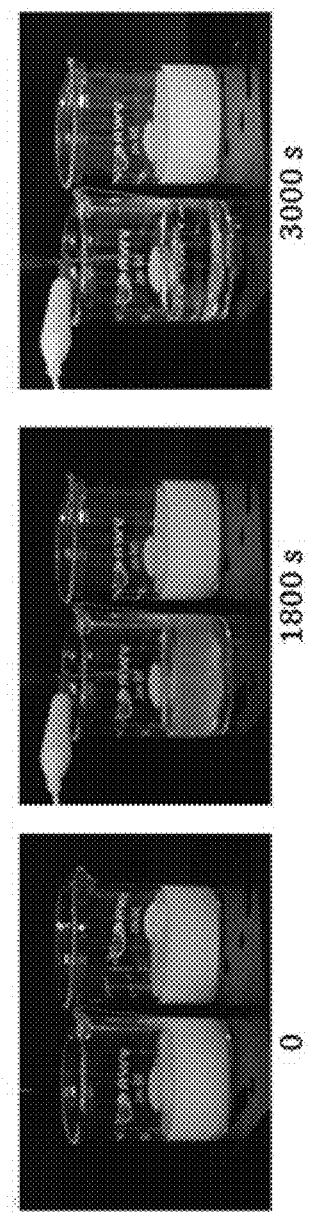
FIG. 11C illustrates unipolar separation of an emulsion including 2% by weight of DI water (shown in white color) in Hexadecane (transparent liquid) stabilized with 1.6% by weight surfactant SPAN80® exposed to a positive DC corona discharge, in accordance with some embodiments of the invention. The applied voltage and corona current were 10.8 kV and 10 µA, respectively.

The concept of like-charge coalescence can be applied to the destabilization of emulsions. FIGS. 11A, 11B and 11C demonstrate like-charge coalescence for a system of two water drops in oil and a water-in-oil emulsion. FIGS. 11A and 11B show the unipolar coalescence of systems of two and three neighboring water drops in oil subjected to unipolar ion injection, respectively. A positive DC corona discharge was established by applying high voltages above the corona discharge thresholds to a sharp emitter electrode. The air adjacent to the emitter electrode was ionized, and a cloud of positive ions was accelerated towards the air/liquid interface due to the strong electric field. The accelerated positive ions were injected into the oil volume. The injected charge was deposited over the surface of the water/oil droplet interface. Since the acquired net charge by the water droplets was proportional to their surface areas, an arbitrary charge difference between two neighboring droplets with different size may be established by applying non-uniform charge injection. Once enough of a charge difference is established, short-range attraction may cause coalescence of like-charge water drops.

FIG. 11C shows like-charge coalescence and unipolar separation of an emulsion comprised of 1.5% wt. DI water in Hexadecane subjected to a corona discharge with different exposure times. In order to stabilize the emulsion, 1.6% wt. Surfactant Span80® was added. The mean diameter of droplets in emulsion was measured to be about 300 nm right before the ionic exposure. The 20 ml of the emulsion poured in two identical beakers. The left beaker was exposed to a corona discharge while the right beaker was left with no exposure. Continuous exposure of the emulsion to the discharge supplies spatially non-uniform volume charge density to the adjacent water droplets. The adjacent water droplets acquire non-uniform positive charge, which promotes like-charge coalescence of water droplets in oil. As a result, the size of the droplets increased as they were exposed to the discharge and the emulsion separation occurred. As shown in FIG. 11C, the cloudy emulsion in the left beaker turned to transparent oil as the water droplets were coalesced and settled down. In the absence of exposure, the cloudy appearance of the right beaker showed negligible change during the same time of experiments suggesting that the coalescence of droplets was minimal as the emulsion was stable during the experiments.

Figure 12A:
FIGS. 12A and 12B show images of like-charged droplets in an emulsion charged by corona discharge in bulk oil and 10% water in 90% oil, respectively, compared with images in FIG. 12C where charging was achieved by tribo-electrification.
Figure 12B:
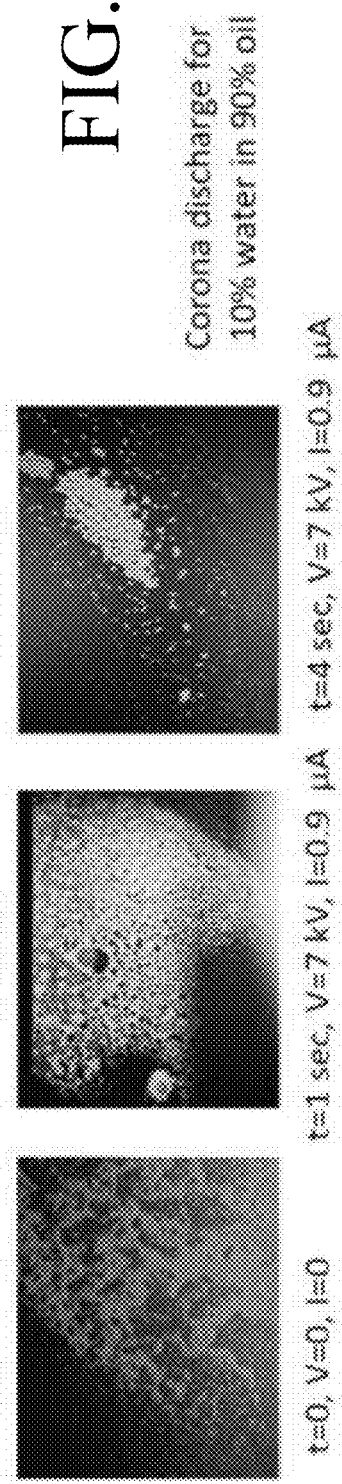
Figure 12C:
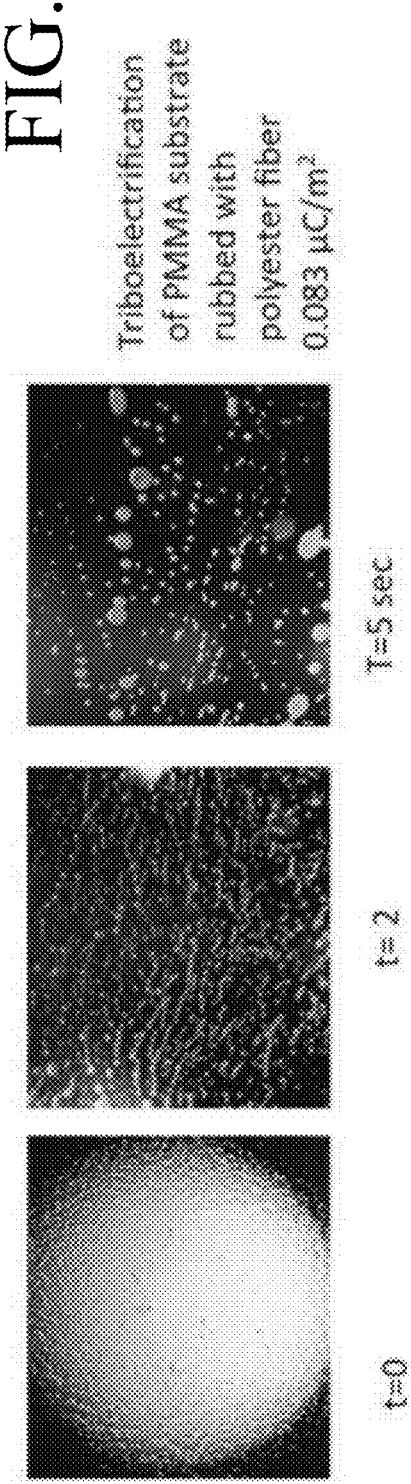

FIGS. 12A, 12B, and 12C show images of like-charged droplets in an emulsion charged by corona discharge, compared with charging by trio-electrification. In order to obtain the tribo-electrification results presented in FIG. 12C, PMMA substrate was rubbed with polyester fiber. Other pairs of materials can be used to produce the charged substrate onto which the emulsion is poured or otherwise introduced. Deposition of emulsion on un-rubbed substrates produces no separation effect since the charge is absent over the substrate. Upon rubbing the dry PMMA substrate, the substrate becomes positively charged while the fiber becomes negative. The charge over the substrate reached a saturation limit and was measured to be ~100 nC/m². Depositing the emulsion on the charged substrate resulted in vigorous separation of the emulsion. A small charge difference between two neighboring droplets causes an attractive force, which causes coalescence of the water droplets. Small charge differences in a dense emulsion may result in destabilization of the emulsion and the desired separation of the phases. These charges can be unipolar on two or many droplets. Without wishing to be bound to any particular theory, a single polarity of charge is sufficient to induce emulsion separation.

Separation of 25% Water-75% Oil

Figure 13:
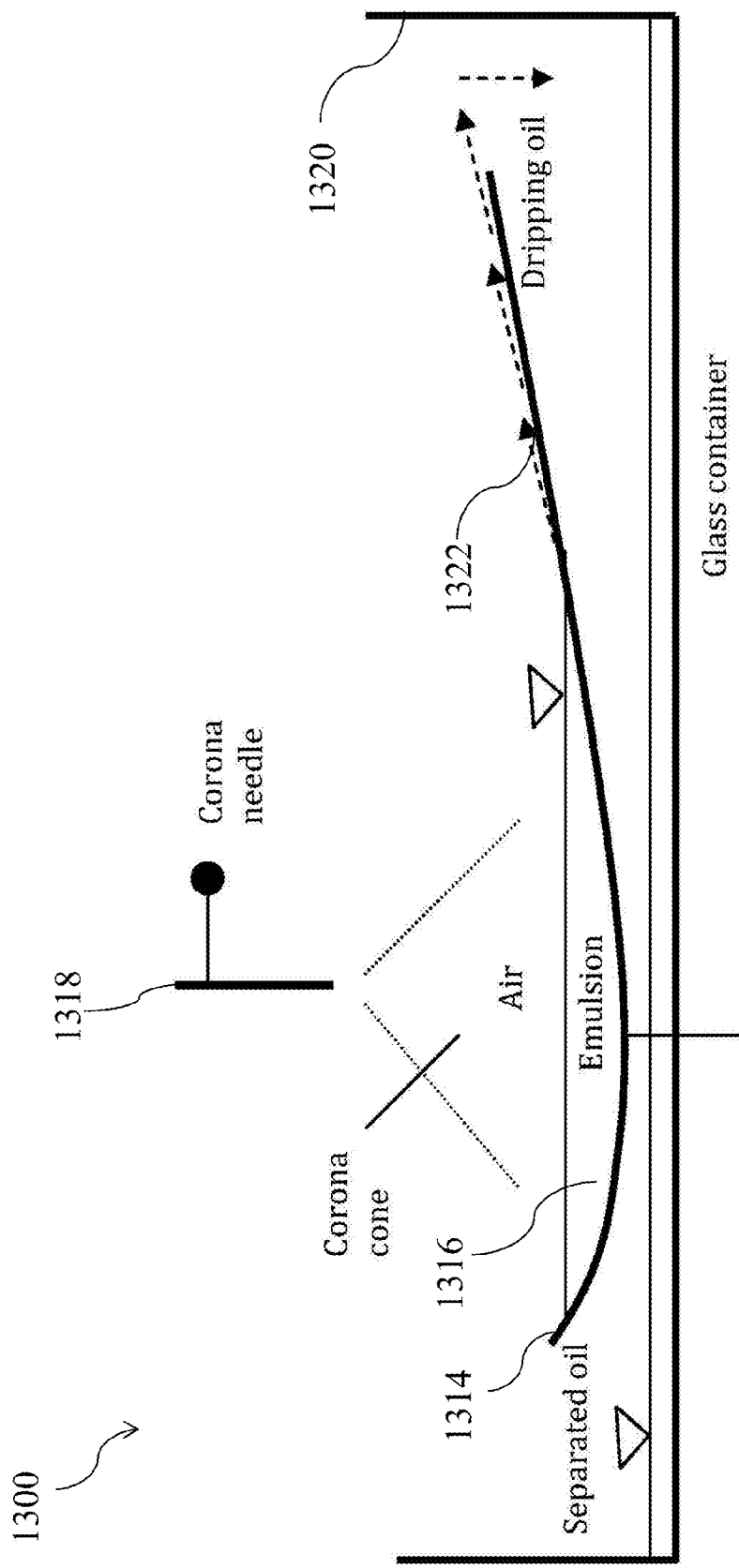
FIG. 13 illustrates an experimental corona discharge separator setup 1300 for separating emulsions having oil as the main phase, in accordance with some embodiments of the invention.

In this example, corona discharge assisted separation of an emulsion was conducted in the presence of electrostatic pumping of the separated oil. As shown in FIG. 13, a curved electrode 1314 was first filled with an emulsion of DI water in Silicone Oil (25 wt. % water, 75 wt. % oil) 1316. The curved electrode 1314 was grounded. A corona needle 1318 was fixed above the emulsion/air interface. The distance between the corona electrode and emulsion interface was tens of millimeters. Therefore, the grounded electrode 1314 had contact with the emulsion 1316 while the corona needle 1318 was located in ambient air and had no ohmic contact with the emulsion 1316. By applying voltage to the needle 1318 above a critical value, a positive corona discharge was established over surface of emulsion 1316 and curved grounded electrode 1314. The corona discharge establishment was confirmed by measuring the corona current.

The cloud of ionized air accelerated toward the emulsion 1316 in the presence of the strong electric field and the emulsion 1316 was positively charged with such ionic bombardment. The water droplets in the bulk oil immediately coalesced. Without wishing to be bound to a theory, non-uniform charging of the droplet is believed to be responsible for coalescing of positive-positive charged droplets. Moreover, the pure separated oil by corona discharge exposure climbed up the curved ramp on the right side of the curved grounded electrode 1314. Corona discharge was used to both separate and pump the pure oil out of the emulsion container 1320. It should be noted that only pure oil could climb up the ramp 1322, while water was not affected. Systems that exploit this differential effect may be implemented, further enhancing separation of phases of the emulsion. The electrostatic pressure cannot be developed over a water droplet, and water (or other aqueous phase) cannot move up the ramp 1322. This is believed to be because the electrical conductivity of water is too high, and the charge relaxation is fast. Therefore, the electrostatic pressure cannot be established over water droplets and pump them up. In contrast, for background oil, charge may stay for a long period of time and electric pressure can be established and pump the separated pure oil up the ramp.

Figure 14B:
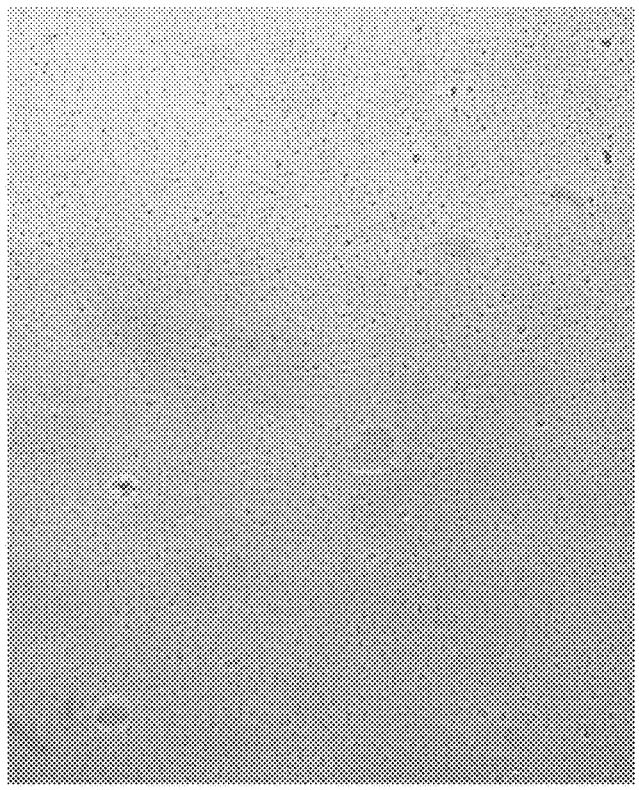
FIG. 14B illustrates oil after corona discharge exposure with an applied voltage of +7 kV and a current of 1 µA, in accordance with some embodiments of the invention. The gap spacing between electrode was 10 mm.
Figure 14A:
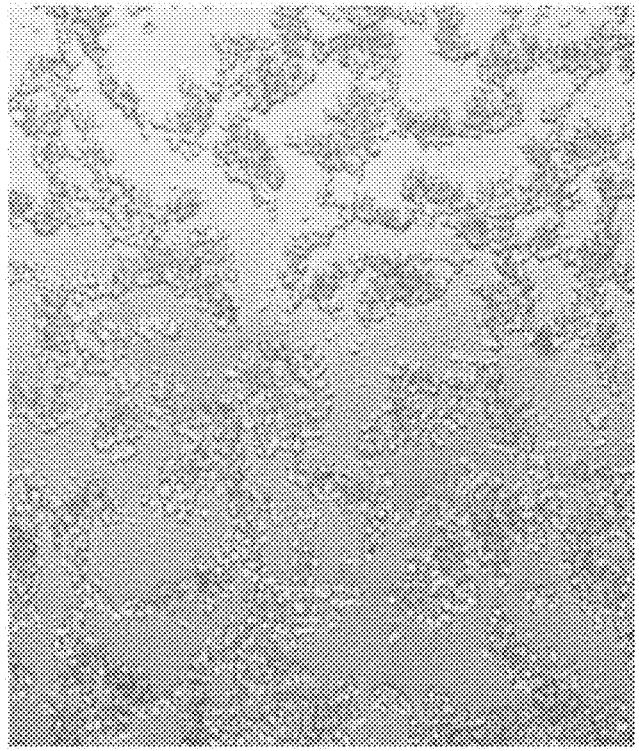
FIG. 14A illustrates a water-in-oil emulsion before corona discharge exposure, in accordance with some embodiments of the invention. The gap spacing between electrode was 10 mm.

Corona discharge of 7 kV-1 µA was applied (7 milliwatt power consumption) for about 10 seconds over the air-emulsion interface to the water-in oil emulsion as can be seen FIG. 14A. FIG. 14B illustrates that the small droplets showed vigorous electro-coalescence. About 90% of the oil content was recovered at this stage. The recovered oil was clear but with minor tracks of water micro-droplets. The purified oil with minor track of water droplets was transferred to the third stage. With 20 seconds of sequential discharge 7 kV-1 µA and then stronger discharge 8.6 kV-2 µA and much stronger 12 kV-3 µA, the accomplished separation shows a separation of 99.9%. The energy consumption for corona discharge-assisted separator with a single needle electrode can be as low as a few miliwatts for lab-size separations. In many embodiments, methods and systems described herein can be used to scale up. For example, with only 40 watt hours (10 kV, 1 µA), one may process 0.1 m³ per/hour.

Figure 15C:
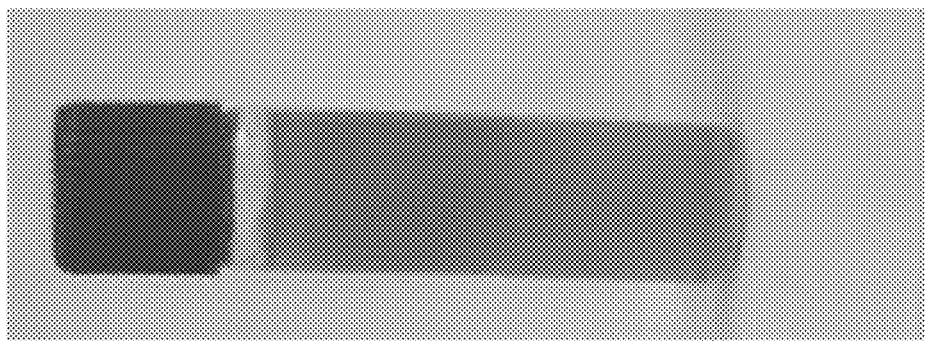
FIG. 15C illustrates an emulsion used for the corona discharge separation process for which the images in FIGS. 15A and 15B are shown, in accordance with some embodiments of the invention.
Figure 15B:
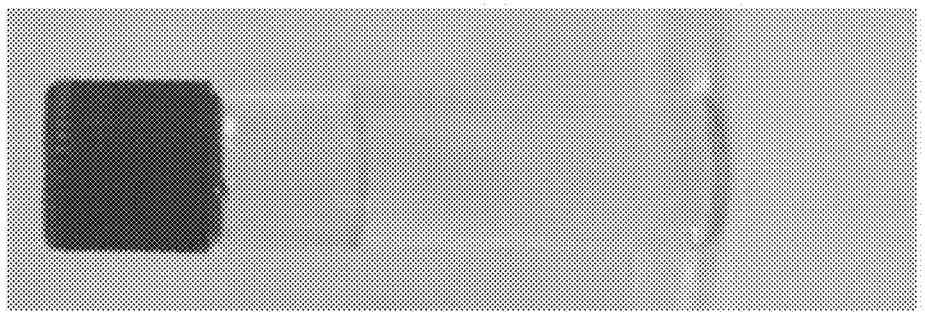
FIG. 15B illustrates silicone oil recovered from an emulsion electrostatically, in accordance with some embodiments of the invention.
Figure 15A:
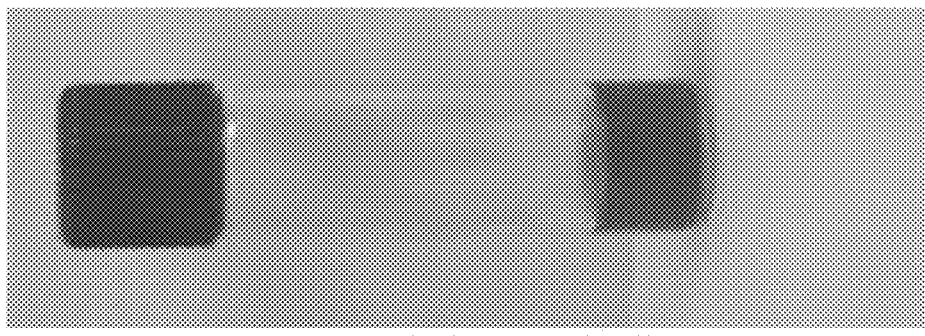
FIG. 15A illustrates water after corona discharge-assisted recovery, in accordance with some embodiments of the invention.

FIG. 15C illustrates an emulsion used for the separation process. FIG. 15B shows silicone oil recovered from the emulsion electrostatically. FIG. 15A illustrates water after corona discharge-assisted recovery.

Separation of 90% Water-10% Oil

Figure 16:
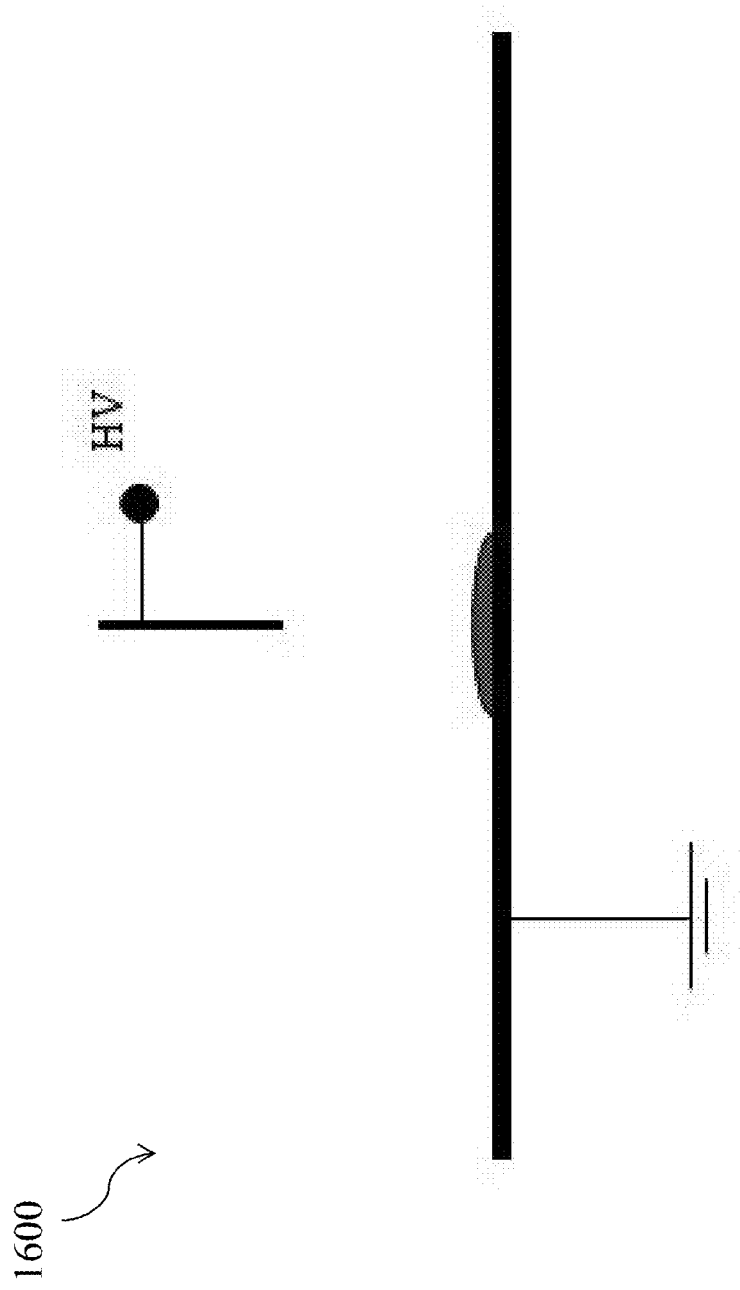
FIG. 16 illustrates an experimental setup 1600 for separating emulsions with water as the main phase, in accordance with some embodiments of the invention.

Setup 1600 shown in FIG. 16 demonstrated corona discharge separation of the emulsion without exploiting the pumping effect. The corona discharge-assisted technique can be used to separate water out of predominately-oil emulsions, where the emulsion contains low concentrations of water and/or small droplet sizes of water emulsified in the oil background. In other embodiments, the corona discharge-assisted technique can be used to separate water and oil phases from emulsions that are predominately water.

The corona discharge exposed emulsion tends to minimize its electrostatic energy when exposed to the discharge. Therefore, the ions may transfer the oil droplet towards the substrate. If the substrate is oleophilic, the oil creates a thin film below the liquid volume. The divergent electric field may drag the oil out of the droplet and cause the water to become separated. It should be noted that when the oil is emulsified in water, the capacitance of the system is large. The charged oil layers are far from the low potential substrate. As the field is exposed, the cloud of ions reaches the water interface and passes through the interface. The oil droplets are now attracted to the substrate to make the capacitance as low as possible. The corona discharge-assisted technique makes separation possible even for emulsions with a fraction of 1% oil in the water. The technique shows promise, particularly where the substrate is flat. The technique seems to be more efficient when implemented in droplet-wise form.

Ion Injection

Figure 17:
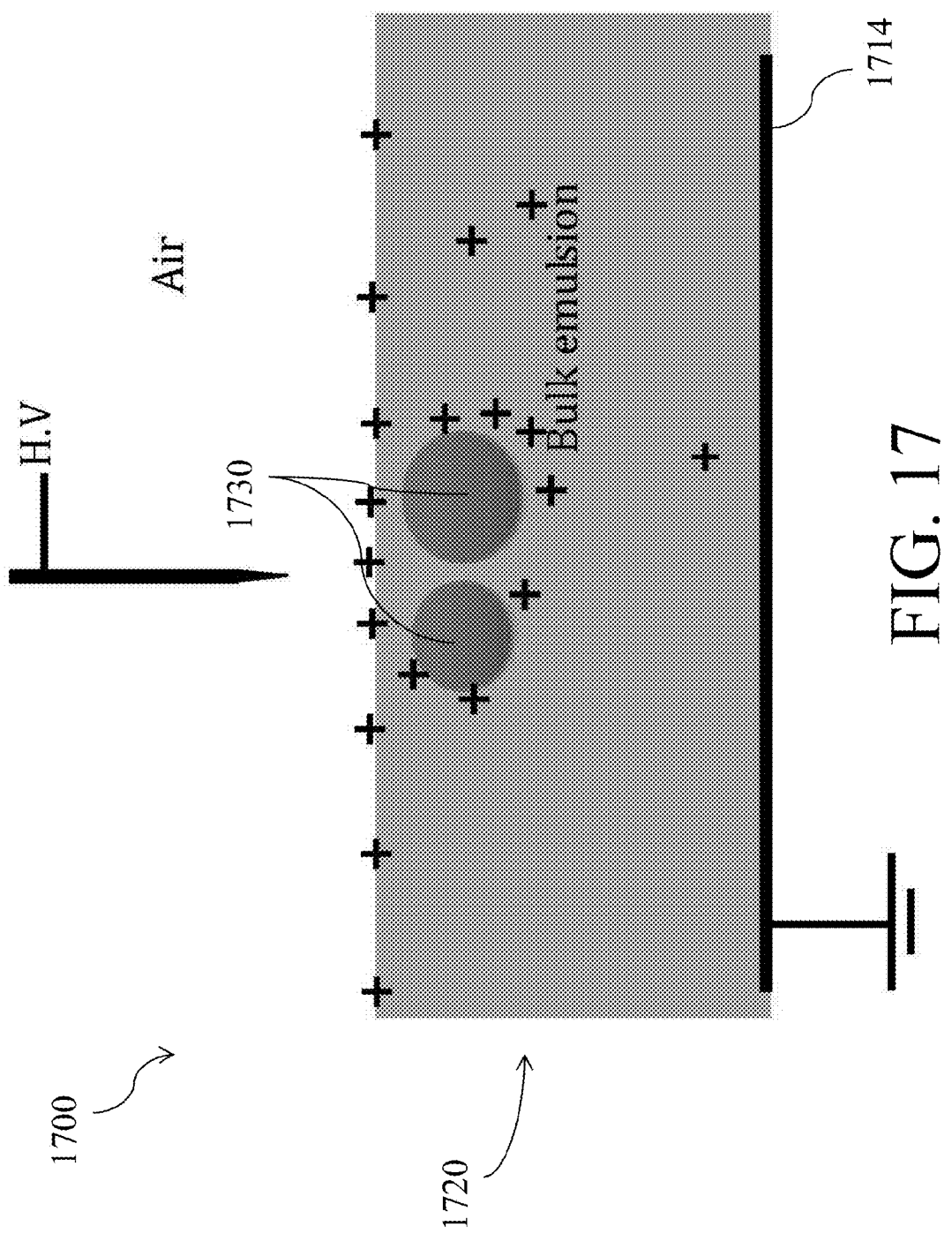
FIG. 17 illustrates an experimental setup 1700 for direct ion injection into emulsions with oil as the main phase, in accordance with some embodiments of the invention.

In the configuration depicted in FIG. 17, the droplets 1730 are directly charged in a bath of emulsion by unipolar ion injection through a corona needle 1718 similar to the embodiment shown in FIG. 13. However, because the container 1720 is not curved, the oil cannot be pumped up. The separated oil stays on the top and is not pumped out by corona discharge. After coalescence, the phases may be separated using standard processes.

In one example, a quartz container was used. The quartz container was filled with the emulsion (10% oil-90% emulsion stabilized by Span® 80 nonionic surfactant). A grounded flat electrode 1714 was fixed at the bottom of the container 1720 as shown in FIG. 17. A corona needle 1718 was fixed above the emulsion/air interface. The gap between the electrode and emulsion/air interface was about 5 mm. The grounded electrode 1714 was a silicon substrate with a native oxide. By increasing the applied voltage, the electric current across the emulsion remained zero and emulsion did not destabilize. Further increasing the applied voltage, at and above the onset of corona discharge threshold, the current was established. This is the signature of the corona discharge. Above this threshold voltage, immediate coalescence between water droplets 1730 was observed, and phase separation (emulsion destabilization) took place. In this example, 7 kV was applied and the total current at this voltage was 0.9 µA. The mean diameter of water droplets 1730 in oil before separation was 50 µm. After corona discharge exposure, depending on exposure time, the mean droplet size grew an order of magnitude larger.

Figure 18:
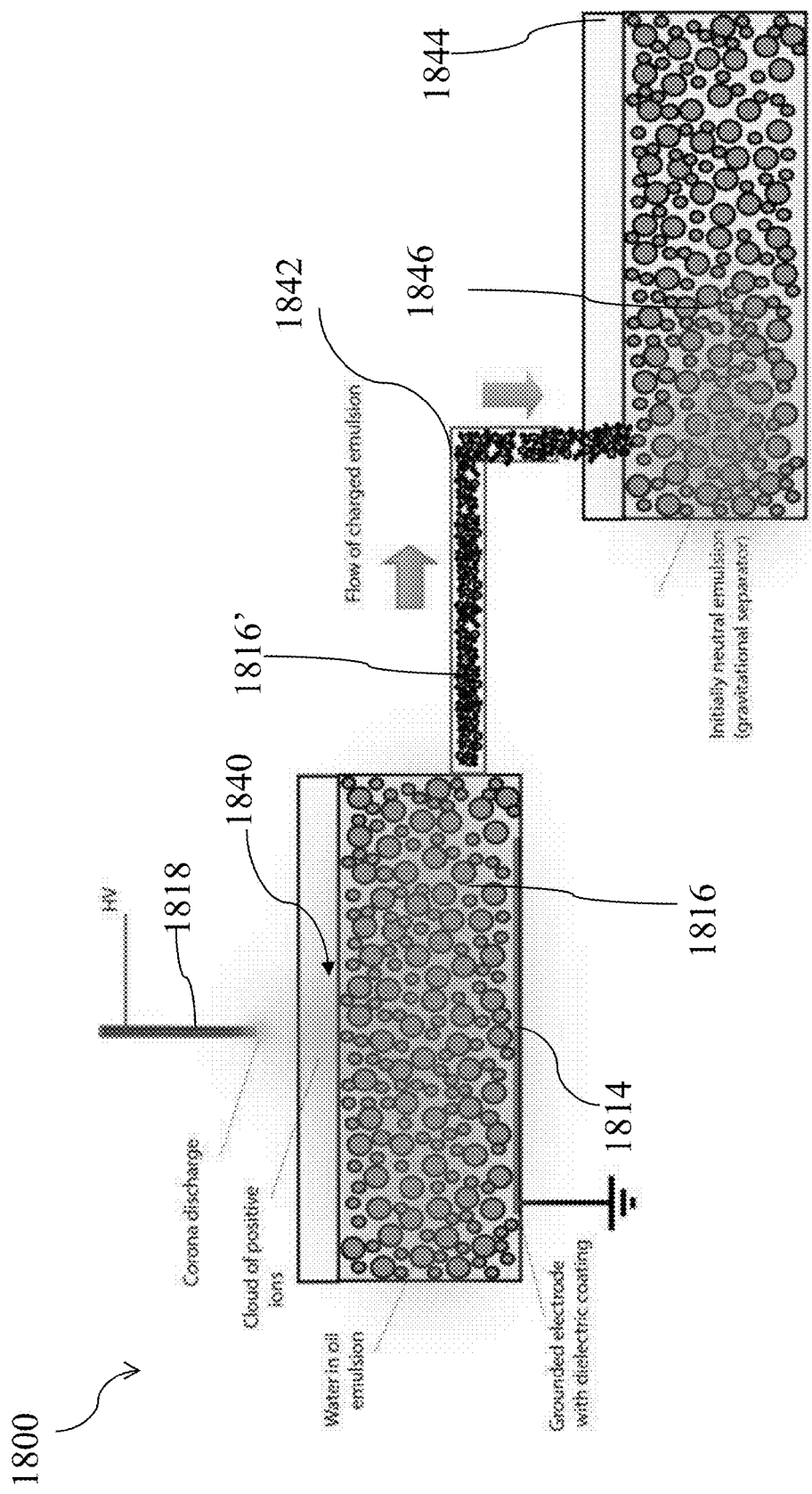
FIG. 18 illustrates an experimental setup 1800 for separation of unipolar emulsions and other mixtures, in accordance with some embodiments of the invention.

Constructive Example—Charging a Portion of Emulsion and Mixing Charged Portion with Neutral Emulsion As shown in FIG. 18, a water in oil emulsion is split up between two containers (or the emulsion or other mixture may initially be present in two containers). A first portion of the emulsion or other mixture is placed into a container 1820. The emulsion 1816 is charged by corona discharge. A corona needle 1818 and a grounded electrode 1814 with dielectric coating are used to establish the corona discharge, as discussed in some embodiments above. The grounded electrode 1814 is in contact with the emulsion 1816. A gaseous medium (e.g., one gas or a mixture of gases discussed above, at any pressure and temperature) is located between the emulsion 1816 and the corona needle 1818. When an electric potential difference between the corona needle 1818 and the grounded electrode 1814 is applied (e.g., by continuous AC or DC discharge or pulsed discharge) above a corona discharge threshold, the imposed electric field becomes strong enough around the sharp tip of the corona needle 1818. such that the surrounding neutral gaseous medium in the electrode separation region become partially ionized, creating a cloud of positive ions 1840, which charges the emulsion 1816. The charged emulsion 1816' is then transported via a conduit 1842 to a second container 1844. The second container includes initially neutral emulsion 1846. The charged emulsion 1816' may then be mixed with the initially neutral emulsion 1846 that needs to be separated.

Figure 19:
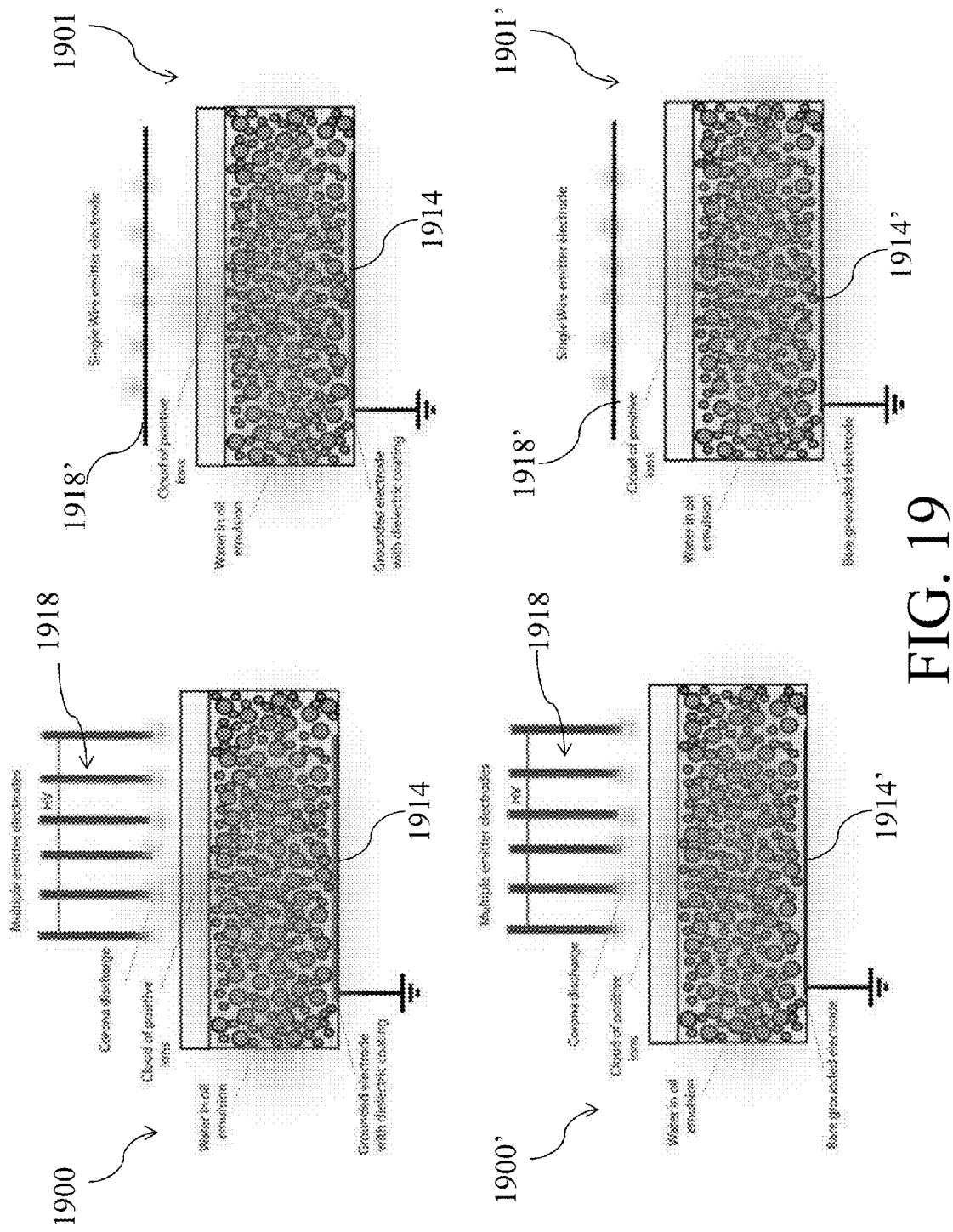
FIG. 19 illustrates exemplary experimental setups 1900, 1900', 1901, 1901' for separation of unipolar emulsions and other mixtures, in accordance with some embodiments of the invention.

Constructive Example—Experimental Setups Using Different Emitter Electrode and Grounded Electrode Configurations Referring now to FIG. 19, the experimental setup 1900 employs multiple emitter electrodes 1918 and a grounded electrode with dielectric coating 1914. The experimental setup 1900' employs multiple emitter electrodes 1918 and a bare grounded electrode 1914'. The experimental setup 1901 employs a single wire emitter electrode 1918' and a grounded electrode with dielectric coating 1914. The experimental setup 1901' employs a single wire emitter electrode 1918' and a bare grounded electrode 1914'.

Figure 20:
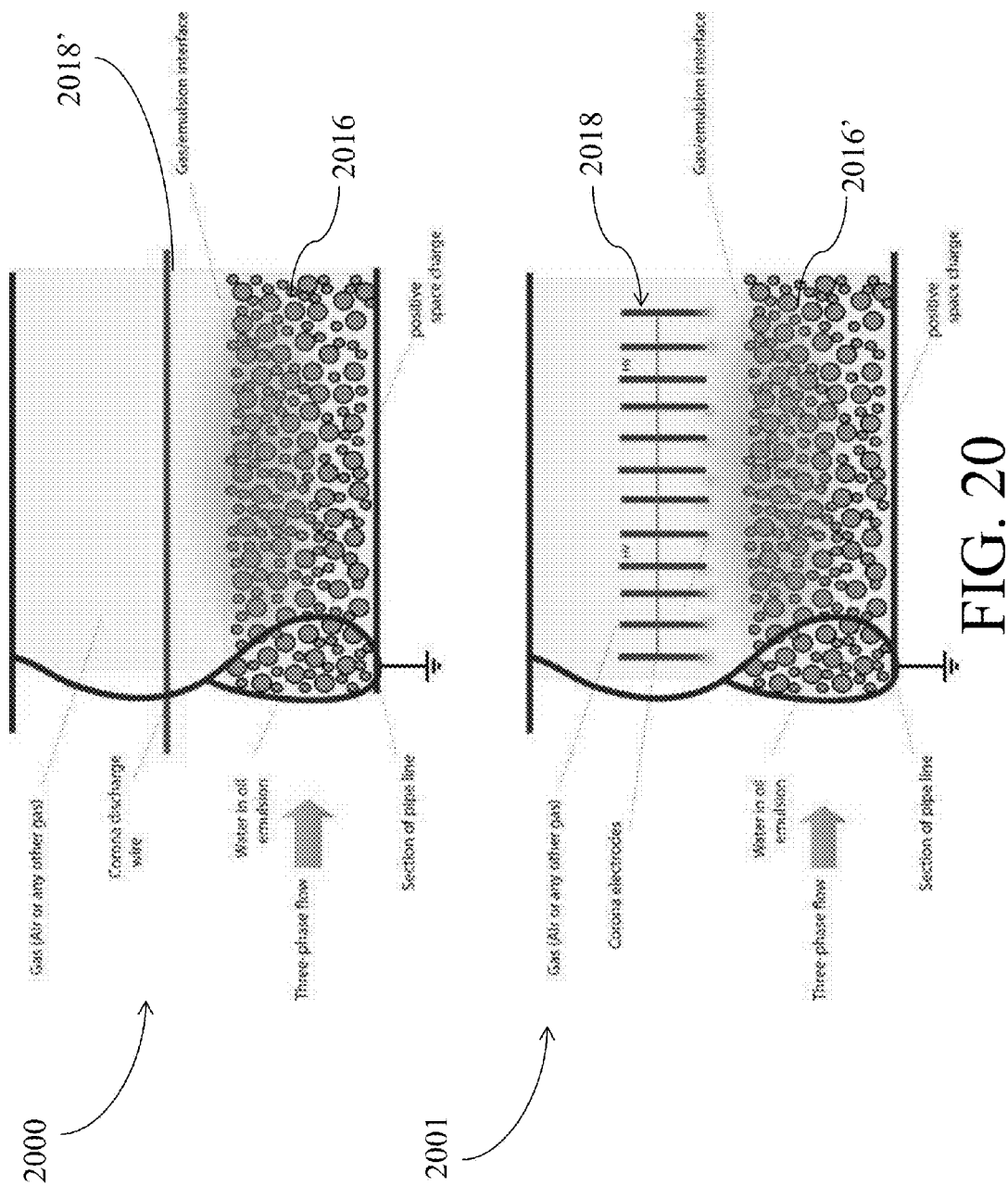
FIG. 20 illustrates experimental setups 2000 and 2001 for separation of unipolar emulsions and other mixtures, in accordance with some embodiments of the invention.

Constructive Example—Experimental Setups Applying Corona Discharge During Transport of an Emulsion or Other Mixture Referring now to FIG. 20, experimental setups 2000 and 2001 are illustrated. Experimental setup 2000 illustrates applying corona discharge during transport of a water in oil emulsion 2016 (other mixtures may be separated as well). A corona discharge wire 2018' is placed above the emulsion 2016 (e.g., the corona discharge wire 2018 is not in contact with the emulsion 2016). In some embodiments, the corona discharge wire 2018' is coated. In some embodiments, the corona discharge wire 2018' is bare. Half (or another suitable portion of the pipe volume) is filled with gas (e.g., air or any gas composition that may effectively increase the effect of current discharge). The experimental setup 2000 allows for an emulsion 2016 (or another mixture) to be separated during transport using corona discharge. Any suitable corona discharge electrode geometries may be used.

Experimental setup 2001 illustrates applying corona discharge during transport of a water in oil emulsion 2016' (other mixtures may be separated as well). Multiple corona electrodes 2018 are placed above the emulsion 2016'. Half (or another suitable portion of the pipe volume) is filled with gas (e.g., air or any gas composition, including mixtures of different gases, that may effectively increase the effect of current discharge). The experimental setup 2001 allows for an emulsion 2016' (or another mixture) to be separated during transport. Any suitable corona discharge electrode geometries may be used.

Constructive Example—Tribo-Electrification Charging Exemplary Setup

Figure 21:
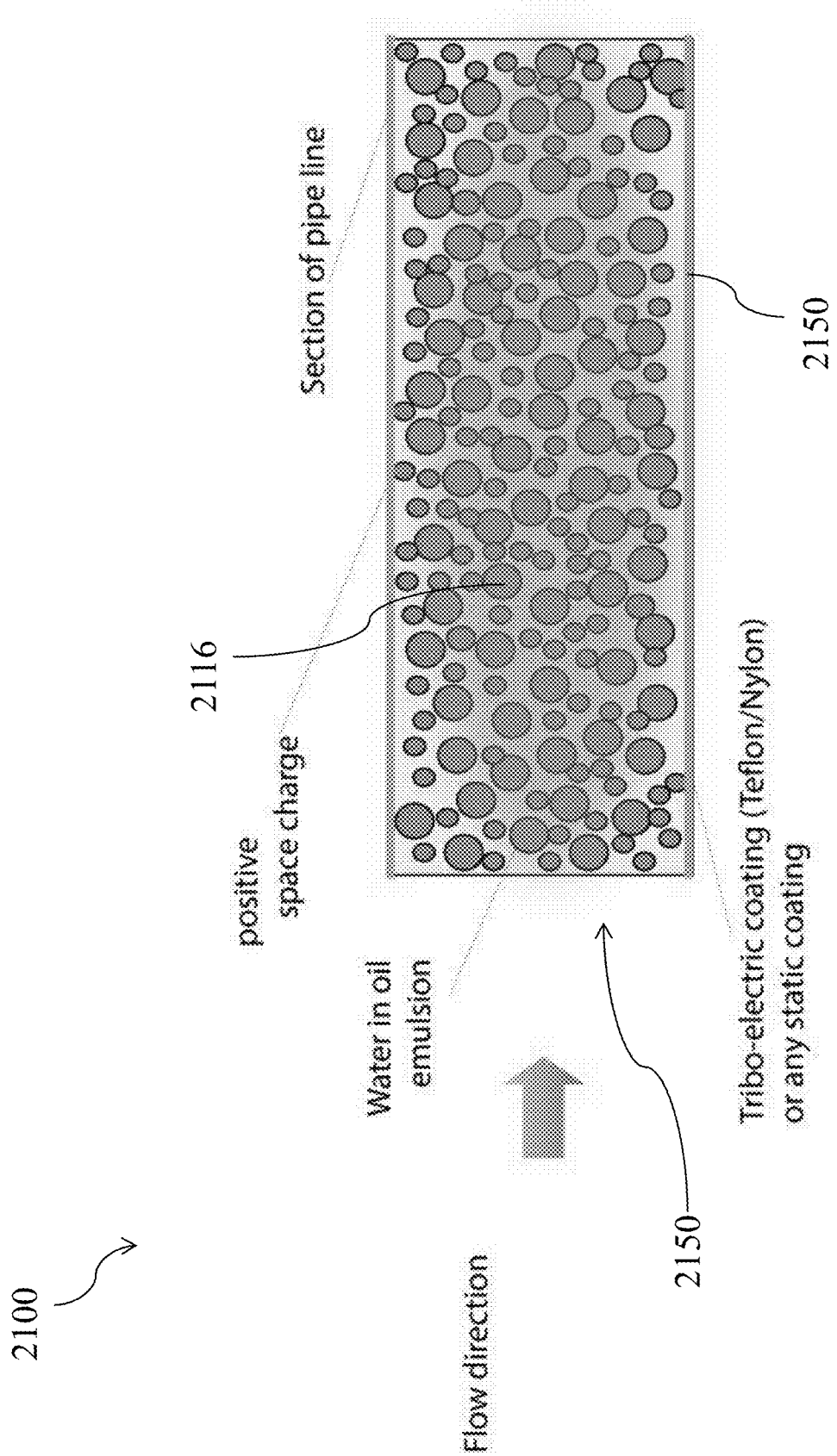
FIG. 21 illustrates an experimental setup 2100 for separation of unipolar emulsions and other mixtures using tribo-electrification charging, in accordance with some embodiments of the invention.

Referring now to FIG. 21, an experimental setup 2100 for separating an emulsion or another mixture during transport is shown. Charge can be introduced to the moving emulsion 2116 by tribo-electrification charging during transport. As shown in FIG. 21, an emulsion 2116 may be separated during transport in a pipe 2150 (or any other conduit capable of transporting an emulsion or another mixture). The interior surface of the pipe 2148 (e.g., the surface that is in contact with the emulsion or other mixture being transported) is coated with a tribo-electric coating that is configured to improve tribo-electrification charging. In some embodiments, the coating 2150 includes a combination of Teflon and Nylon (in suitable proportions). In some embodiments, the coating 2150 is a static coating of a suitable type (e.g., suitable for improving tribo-electrification charging). Unipolar charge in the volume of the mixture can promote the separation of the emulsion 2116 during the transport as it passes through the pipe 2150. Unipolar separation can be completed completely or in part during the transport of the emulsion through the pipe 2150.

Constructive Example—Ionized Gas Exemplary Setup

Figure 22:
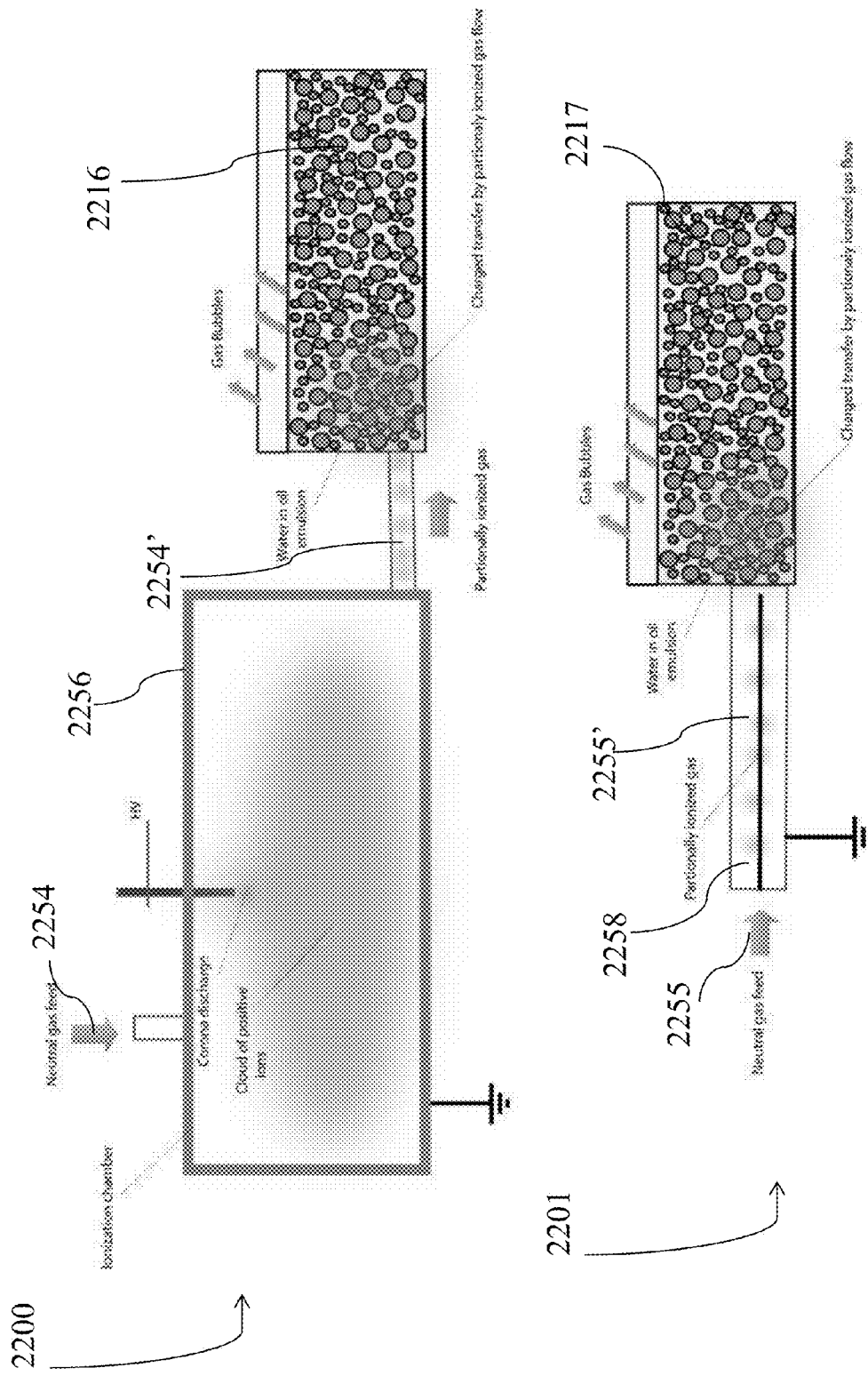
FIG. 22 illustrates experimental setups 2200 and 2201 for introducing a charge to an emulsion or other mixture, in accordance with some embodiments of the invention.

Referring now to FIG. 22, an experimental setup 2200 for separating emulsions or other mixtures is shown. Neutral gas (e.g., gas having no net charge) 2254 is fed into an ionization chamber 2256. The neutral gas 2254 is then ionized in the ionization chamber 2256. In some embodiments, the neutral gas 2254 is ionized by using corona discharge (e.g., as discussed for other corona discharge embodiments above). The partially ionized gas 2254' carrying a unipolar charge is then introduced into an emulsion or other mixture 2216 (e.g., from one location or from multiple locations). In some embodiments, the partially ionized gas 2254' passes through the emulsion or other mixture 2216.

The experimental setup 2201 illustrates another illustrative embodiment for introducing a charge to an emulsion or another mixture 2217 to be separated. Neutral gas 2255 is fed into a pipe or another conduit 2258. The neutral gas 2255 is ionized during transport through the pipe or another conduit 2258 (e.g., ionized via corona discharge). Partially ionized gas 2255' is then injected into the emulsion or another mixture 2217 (from a single location or from multiple locations). In some embodiments, the partially ionized gas 2255' passes through the emulsion or other mixture 2217.

In some embodiments, to increase the interface of the ionized gas bubbles with the emulsion or other mixture 2216 or 2217, the size of the bubbles can be decreased. In some embodiments, the emulsion or other mixture 2216 or 2217 can be physically agitated prior to the entrance of the bubbles into the emulsion or other mixture 2216 or 2217. The bubbles can be injected into the emulsion or other mixture 2216 or 2217 from a single location or from multiple locations. The bubbles may be injected from underneath the emulsion or other mixture 2216 or 2217. In other embodiments, the bubbles may be injected from above the emulsion or other mixture 2216 or 2217.

Other Embodiments

Embodiments and examples described herein are for illustration purpose only not for limitation. The scope of the invention is illustrated by the claims attached hereto and various changes and modifications within the scope of the invention will be apparent to those skilled in the art.

What is claimed is:

1. A method for separating two or more phases of emulsion mixture, the method comprising the steps of:
    (a) providing the mixture with a net and unipolar charge, thereby inducing coalescence of like-phase and like-charge droplets therein and producing two or more consolidated phases wherein the coalescence of the like-phase and like-charge droplets is only induced by applying the net and unipolar charge to the emulsion via tribo-electrification or introduction of the mixture to a substrate having a net and unipolar charge that is positive or negative, wherein the substrate is charged by tribo-electrification; and (b) collecting the two or more consolidated phases.

2. The method of claim 1, wherein the separating is carried out during transport of the mixture.

3. The method of claim 1, wherein step (a) comprises providing a portion of the mixture with a unipolar charge, the method further comprising mixing the charged portion of the mixture into the remaining portion of the mixture, thereby enhancing coalescence of like-phase droplets therein and producing, or enhancing the production of, two or more consolidated phases; and (b) collecting the two or more consolidated phases.

4. The method of claim 1, wherein step (a) comprises injecting, spraying, or otherwise introducing a substance into the mixture, thereby enhancing coalescence of like-phase droplets therein and producing, or enhancing the production of, the two or more consolidated phases.

5. The method of claim 4, further comprising agitating the mixture prior to step (a).

6. The method of claim 1, wherein the mixture, while maintaining a net and unipolar charge, comprises a combination of species having positive and negative charges.

7. The method of claim 1, wherein the mixture comprises a plurality of liquid phases and/or wherein the mixture comprises one or more members selected from the group consisting of particles, proteins, DNA, RNA, and cells, and/or wherein the mixture comprises a liquid with low electrical conductivity.

8. The method of claim 1, wherein the mixture comprises an aqueous phase, and the aqueous phase has a salt content of at least about 0.5M.

9. The method of claim 1, wherein, prior to introduction of the net and unipolar charge, the mixture comprises a phase of droplets having average droplet diameter less than or equal to about 1000 micrometers in diameter, and wherein the droplets coalesce after introduction of the net and unipolar charge.

10. The method of claim 1, wherein the mixture is a two-phase emulsion comprising an aqueous phase and a non-aqueous phase, wherein the aqueous phase is less than or equal to 50 wt. % of the emulsion and/or wherein the non-aqueous phase is less than or equal to 50 wt. % of the emulsion.

11. The method of claim 1, wherein the mixture is a three-phase mixture.

12. The method of claim 1, wherein the mixture comprises a liquid phase, a solid phase, and a gas phase.

13. The method of claim 1, wherein the mixture is a bubble-in-oil mixture or a foam-in-oil mixture and/or wherein the mixture comprises an emulsifier.

14. The method of claim 1, wherein the mixture comprises at least one phase having a salt content of at least about 0.5M.

15. The method of claim 1, wherein the mixture comprises an oil, the oil having an electrical conductivity between about $10^{-14}$ S/m (highly insulating) to about $10^{-5}$ S/m (highly conducting).

16. The method of claim 1, wherein the mixture has an electrical conductivity between about $10^{-7}$ S/m to about 100 S/m.

* * * * *